(12) United States Patent
Eddie et al.

(10) Patent No.: US 10,760,236 B2
(45) Date of Patent: Sep. 1, 2020

(54) SYSTEM AND METHOD FOR REAL-TIME DISPLACEMENT CONTROL USING EXPANSIVE GROUTING TECHNIQUES

(71) Applicant: Redrock Ventures B.V., Amsterdam (NL)

(72) Inventors: Colin Michael Eddie, Warwickshire (GB); Roland John Caldbeck, Southport (GB)

(73) Assignee: Redrock Ventures B.V., Amsterdam (NL)

( * ) Notice: Subject to any disclaimer, the term of this patent is extended or adjusted under 35 U.S.C. 154(b) by 0 days.

(21) Appl. No.: 15/843,476

(22) Filed: Dec. 15, 2017

(65) Prior Publication Data

US 2019/0186095 A1    Jun. 20, 2019

(51) Int. Cl.
*E02D 3/12* (2006.01)
*G01N 33/24* (2006.01)

(52) U.S. Cl.
CPC ............... *E02D 3/12* (2013.01); *G01N 33/24* (2013.01); *E02D 2250/003* (2013.01); *E02D 2300/0006* (2013.01); *E02D 2300/007* (2013.01); *E02D 2300/0045* (2013.01)

(58) Field of Classification Search
CPC .. E02D 3/12; E02D 35/00; E02D 5/46; E01C 23/10
See application file for complete search history.

(56) References Cited

U.S. PATENT DOCUMENTS

| 4,567,708 | A | 2/1986 | Haekkinen | |
|---|---|---|---|---|
| 6,634,831 | B2 | 10/2003 | Canteri | |
| 6,801,814 | B1* | 10/2004 | Wilson | E02D 3/12 175/71 |
| 9,200,422 | B2* | 12/2015 | Hakkinen | E02D 5/46 |
| 2007/0031195 | A1* | 2/2007 | Canteri | E02D 3/12 405/240 |

(Continued)

FOREIGN PATENT DOCUMENTS

| EP | 1536069 A1 | 6/2005 |
|---|---|---|
| EP | 1956147 * | 8/2008 |

(Continued)

OTHER PUBLICATIONS

International Search Report issued in PCT Application Serial No. PCT/EP2017/083169 dated Oct. 5, 2018.

*Primary Examiner* — Sean D Andrish
(74) *Attorney, Agent, or Firm* — Mark H. Whittenberger; Heath M. Sargeant; Holland & Knight LLP

(57) ABSTRACT

The present disclosure relates to a method for real-time compensation for ground movements which would otherwise adversely affect an existing built environment. Embodiments may include providing a plurality of holes in soil for the injection of a substance that expands as a consequence of a chemical reaction. The plurality of holes may be located between a source of movement and an asset to be protected. Embodiments may also include injecting, in at least one of the plurality of holes, the substance and monitoring, in real-time, at least one of movement of the soil or the asset to be protected. Real-time monitoring may occur during an activity that is causing the ground movements. Embodiments may further include obtaining real-time monitoring data, based upon, at least in part, the monitoring.

29 Claims, 27 Drawing Sheets

(56) References Cited

U.S. PATENT DOCUMENTS

| | | | |
|---|---|---|---|
| 2009/0155002 A1* | 6/2009 | Hakkinen | E02D 3/12 405/263 |
| 2009/0304457 A1 | 12/2009 | Shimada et al. | |
| 2010/0263858 A1* | 10/2010 | Chauffe | E21B 33/1208 166/179 |
| 2013/0129423 A1* | 5/2013 | Hakkinen | E02D 27/34 405/128.7 |
| 2017/0073919 A1* | 3/2017 | Barron | E02D 3/12 |

FOREIGN PATENT DOCUMENTS

| | | |
|---|---|---|
| EP | 1956147 A1 | 8/2008 |
| JP | 2006257281 A | 9/2006 |
| JP | 2011226250 A | 11/2011 |

* cited by examiner

SYSTEM AND METHOD FOR REAL-TIME DISPLACEMENT CONTROL USING EXPANSIVE GROUTING TECHNIQUES

DISCUSSION OF THE RELATED ART

Any building requires the foundation soil to have a sufficient bearing capacity to support it. Otherwise, the settling of the foundation soil leads to the failure of the overlying building, regardless of whether the settling occurs in the uppermost or in the deep layers.

Before erecting any building, the bearing capacity of the soil is therefore estimated according to the weight or load which the building will apply to the soil, even using, if necessary, appropriate soil research, such as for example geological and geotechnical research.

In order to ensure the stability of the structure, the optimum dimensions of the foundations and their rigidity are calculated and the depth of the foundations is also determined, adequately balancing their weight in relation to the bearing capacity of the soil and always maintaining a good safety margin. In case of error, the building may in fact fail.

Often, however, the bearing capacity of the foundation soil is not sufficient, since the soil is compressible, as in the case of filled-in land, non-consolidated land, land with decomposing organic layers, peaty land, swampy land, land with considerable variations in water content, flooded or washed-out land with voids or with non-uniform or insufficiently aggregated masses, land with interstitial voids, et cetera; or the building is very heavy and requires a greater bearing capacity than the actual bearing capacity of the foundation soil.

Various conventional systems ensure in any case the stability of the building. Generally, these systems tend to directly transfer the weight of the building to the deeper and adequately solid soil layers or to spread the load over a wide ground surface, such as for example the method consisting in driving piles or micropiles and the like into the foundation soil. This method can be used both before and after construction. However, the driving of piles and micropiles or the like after the construction of the building is extremely complicated and expensive.

Conventional methods also cope with any subsidence of the building after its construction, such as for example the method described in U.S. Pat. No. 4,567,708, which entails the injection of an expandable substance beneath the building to fill the interstices which have formed and have caused the subsidence and in order to recover the subsidence of the building, or other lifting methods.

In the method disclosed in the above-cited patent, as well as in other lifting systems, however, the foundation soil is not treated; at the most, one acts on the surface layers of the soil, and therefore if the underlying soil has not settled enough, further subsequent subsidence of said building will occur over time.

SUMMARY

In one or more embodiments of the present disclosure, a method for real-time compensation for ground movements which would otherwise adversely affect an existing built environment is provided. Embodiments may include providing a plurality of holes in soil for the injection of a substance that expands as a consequence of a chemical reaction. The plurality of holes may be located between a source of movement and an asset to be protected. Embodiments may also include injecting, in at least one of the plurality of holes, the substance and monitoring, in real-time, at least one of movement of the soil or the asset to be protected. Real-time monitoring may occur during an activity that is causing the ground movements. Embodiments may further include obtaining real-time monitoring data, based upon, at least in part, the monitoring.

One or more of the following features may be included. The method may include displaying, at a graphical user interface, at least a portion of the real-time monitoring data. Monitoring may include monitoring at least one of displacement, stress, strain or temperature. Monitoring may further include taking measurements prior to injecting the substance, during injecting the substance, and/or after injecting the substance. The substance may be selected from the group consisting of a polymer, an expanding resin or an organically incrystallizable, chemically expanding multicomponent substance. The method may also include adjusting, in real-time, the injecting based upon, at least in part, the monitoring in real-time. The method may further include installing above ground instrumentation to measure movement of the ground and/or installing below ground instrumentation to measure movement of the ground. The method may further include transmitting, from at least one measurement instrument to a computing device, the real-time monitoring data associated with the injection of the expanding substance. In some embodiments, providing the plurality of holes may include installing a plurality of injection boreholes in a pre-determined configuration. The method may further include selecting the substance, wherein the substance is selected from the group consisting of a polymer, an expanding resin or an organically incrystallizable, chemically expanding multicomponent substance. The method may also include preparing a mitigation strategy in advance of the activity and/or selecting an injection strategy compatible with ground conditions or a ground movement mitigation strategy.

In another embodiment of the present disclosure, a construction method is provided. The method may include drilling a plurality of holes in a predetermined location and injecting, in at least one of the plurality of holes, a substance that expands as a consequence of a chemical reaction. The method may further include monitoring, during at least one of the injecting or expansion of the substance, at least one of movement associated with the predetermined location or an asset to be protected, wherein monitoring occurs during an activity that is causing the ground movements. The method may also include transmitting monitoring data, based upon, at least in part, the monitoring.

One or more of the following features may be included. The method may include inserting one or more injection tubes into each of the plurality of holes. The method may also include displaying, at a graphical user interface, at least a portion of the monitoring data. In some embodiments, monitoring may include monitoring at least one of displacement, stress, strain or temperature. The method may further include adjusting, in real-time, the injecting based upon, at least in part, the monitoring.

Additional features and advantages of embodiments of the present disclosure will be set forth in the description which follows, and in part will be apparent from the description, or may be learned by practice of embodiments of the present disclosure. The objectives and other advantages of the embodiments of the present disclosure may be realized and attained by the structure particularly pointed out in the written description and claims hereof as well as the appended drawings.

It is to be understood that both the foregoing general description and the following detailed description are exemplary and explanatory and are intended to provide further explanation of embodiments of the invention as claimed.

BRIEF DESCRIPTION OF THE DRAWINGS

The accompanying drawings, which are included to provide a further understanding of embodiments of the present disclosure and are incorporated in and constitute a part of this specification, illustrate embodiments of the present disclosure and together with the description serve to explain the principles of embodiments of the present disclosure.

DETAILED DESCRIPTION

Figure 1:
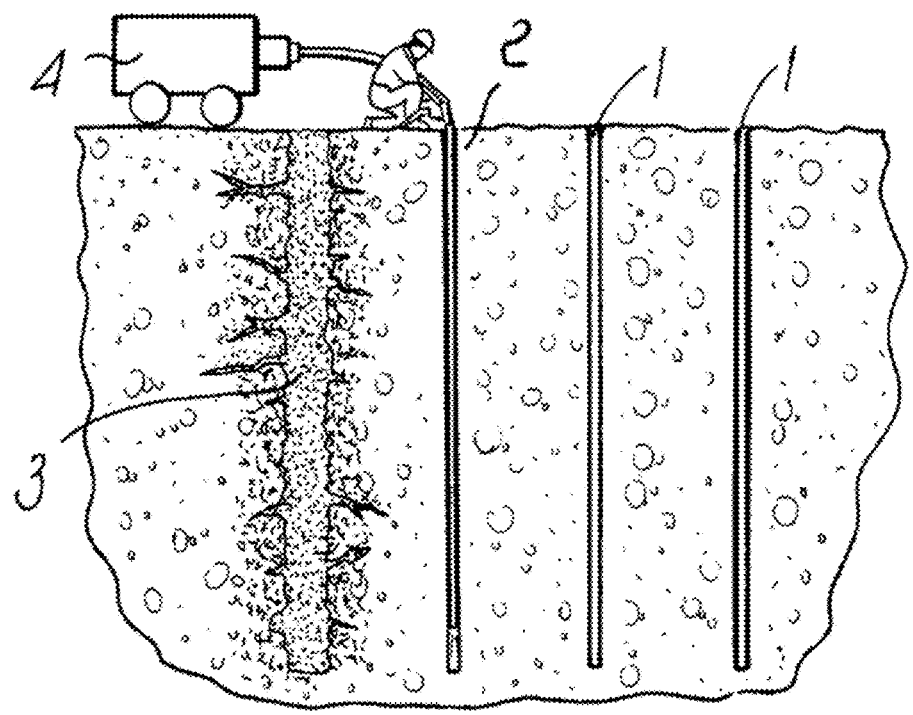
FIG. 1 is a schematic view of the injection of the expandable substance through holes formed in the soil.

Referring to FIG. 1 an embodiment of a construction process is provided. The process may substantially consist of forming in the soil a plurality of holes 1 which, if one must act on existing buildings, may or may not pass through the foundation, at different depths and preferably with a distance between two contiguous holes 1 which can vary between 0.5 m and 3 m. The holes 1 can have variable dimensions according to requirements and can be provided substantially vertically or at an angle with respect to the vertical. The depth of the holes may also vary according to requirements, as will become apparent hereinafter.

In some embodiments, tubes 2 may then be inserted or driven into the holes 1 and a substance 3 expanding as a consequence of a chemical reaction between the components, with a potential volume increase of at least five times the volume of the substance before expansion, may be injected into the soil through said tubes. The expression "potential volume increase" relates to the volume increase of the substance as a consequence of an expansion occurring unhindered at atmospheric pressure. High expansion coefficients of 20-25 times the initial volume or even higher such as 30-33 may be used.

In some embodiments, the expandable substance may be conveniently constituted by a mixture of expandable polyurethane foam, for example, a closed-cell polyurethane foam. This substance can be constituted, for example, by a two-part foam mixed inside a mixing unit 4 connected to the injection tubes 2. The first component can be a mixture of polyols comprising a polyether polyol and/or a polyester polyol, a catalyst, such as RESINOL AL 643, and water. The water in the composition may be 3.44% by weight. The second component can be an isocyanate methylene diphenyl dissocyanate (MDI), such as URESTYL 10. The mixing of these two components produces an expandable polyurethane foam the density whereof, at the end of expansion, varies according to the resistance opposed by the soil adjacent to the injection region.

In some embodiments, the mixture may expand up to about 33 times its initial volume and the reaction time is of about 3-120 seconds, as it appears from the technical specifications of the manufacturer. It is of course also possible to use other expandable substances having similar properties without thereby abandoning the scope of the protection of the present invention.

Figure 2:
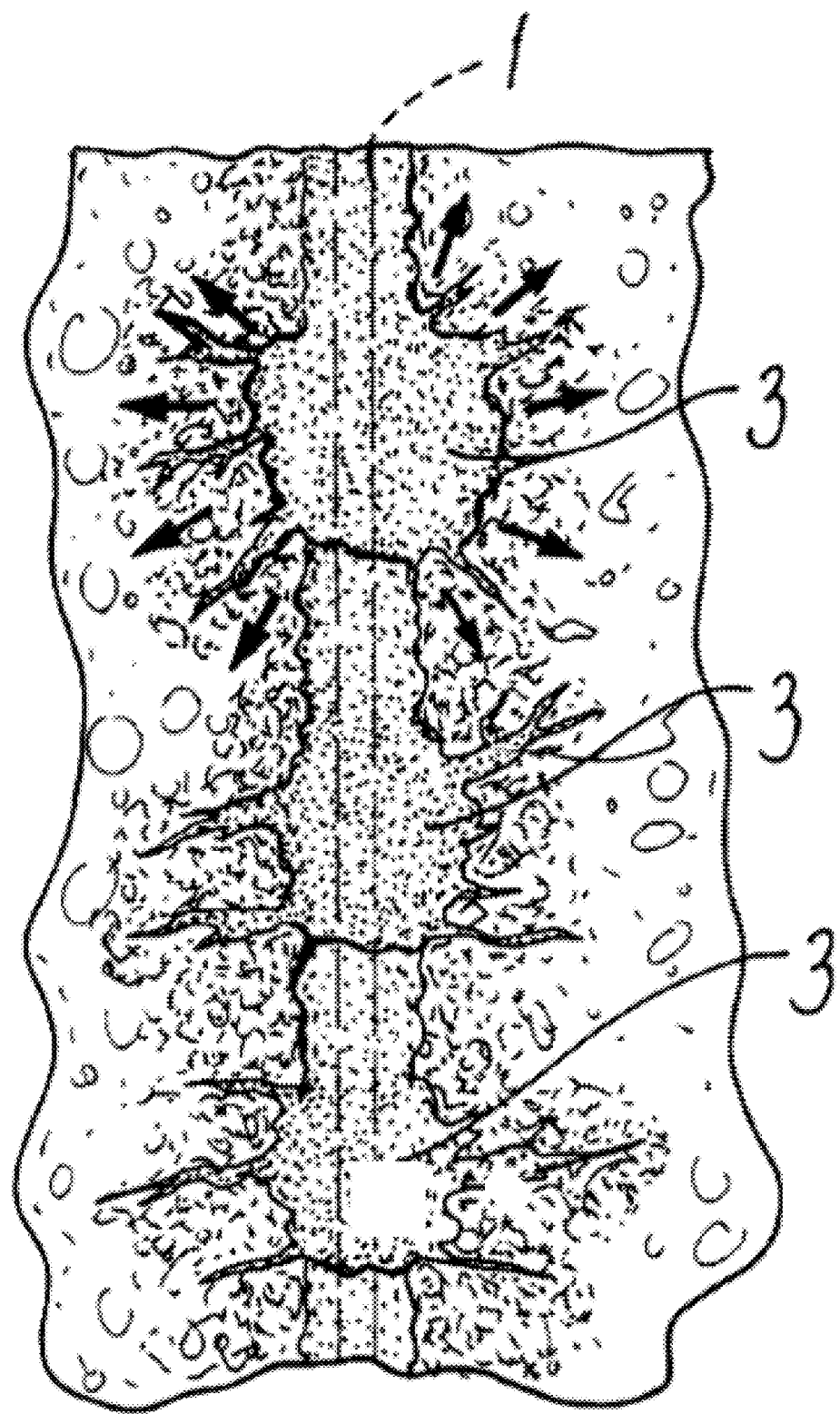
FIGS. 2 and 3 are views of the result of the expansion of the expandable substance when the substance is injected whilst the tube used for injection is gradually retracted upwards, respectively with pauses at intermediate depth levels or with a continuous motion.
Figure 3:
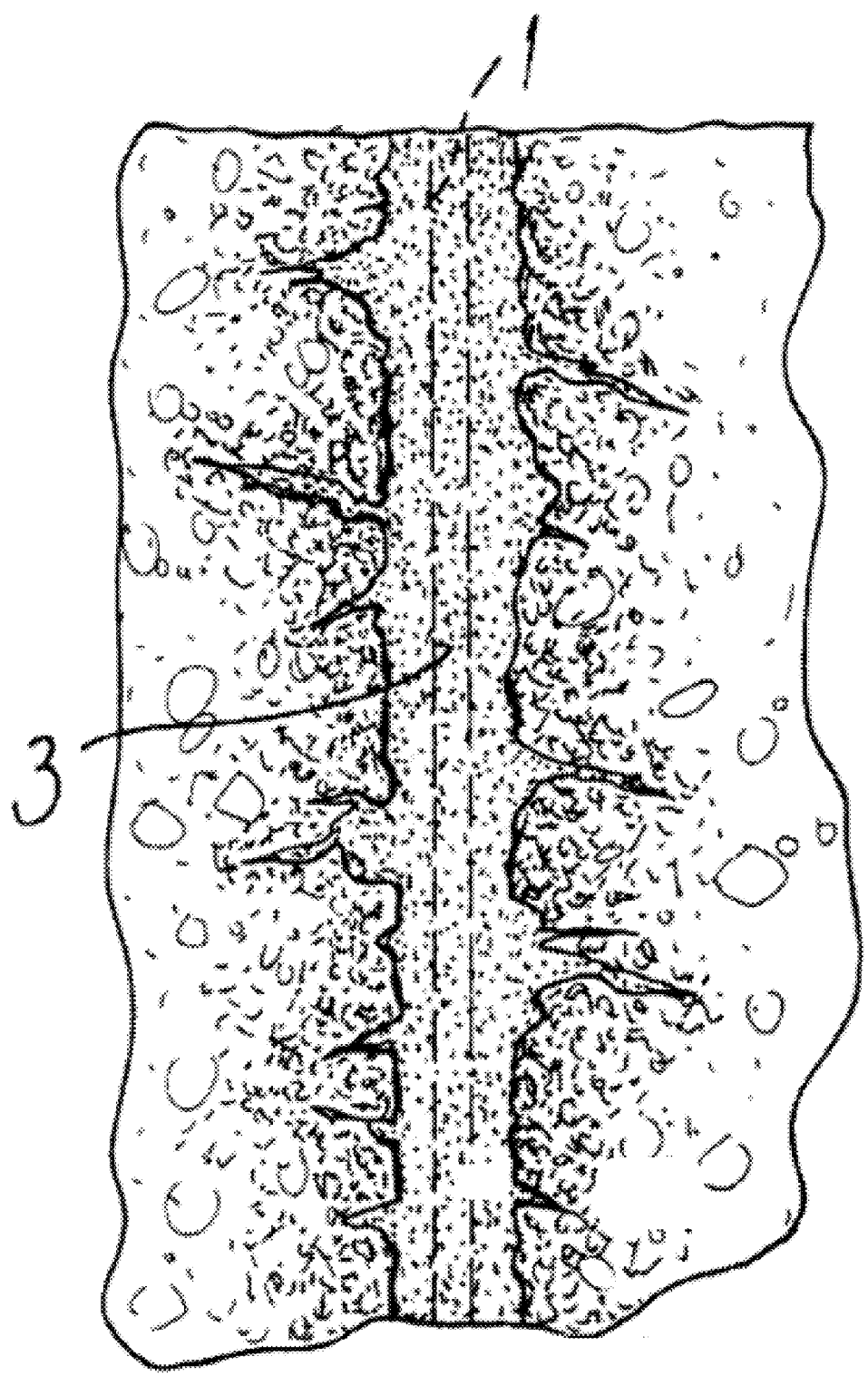
Figure 4:
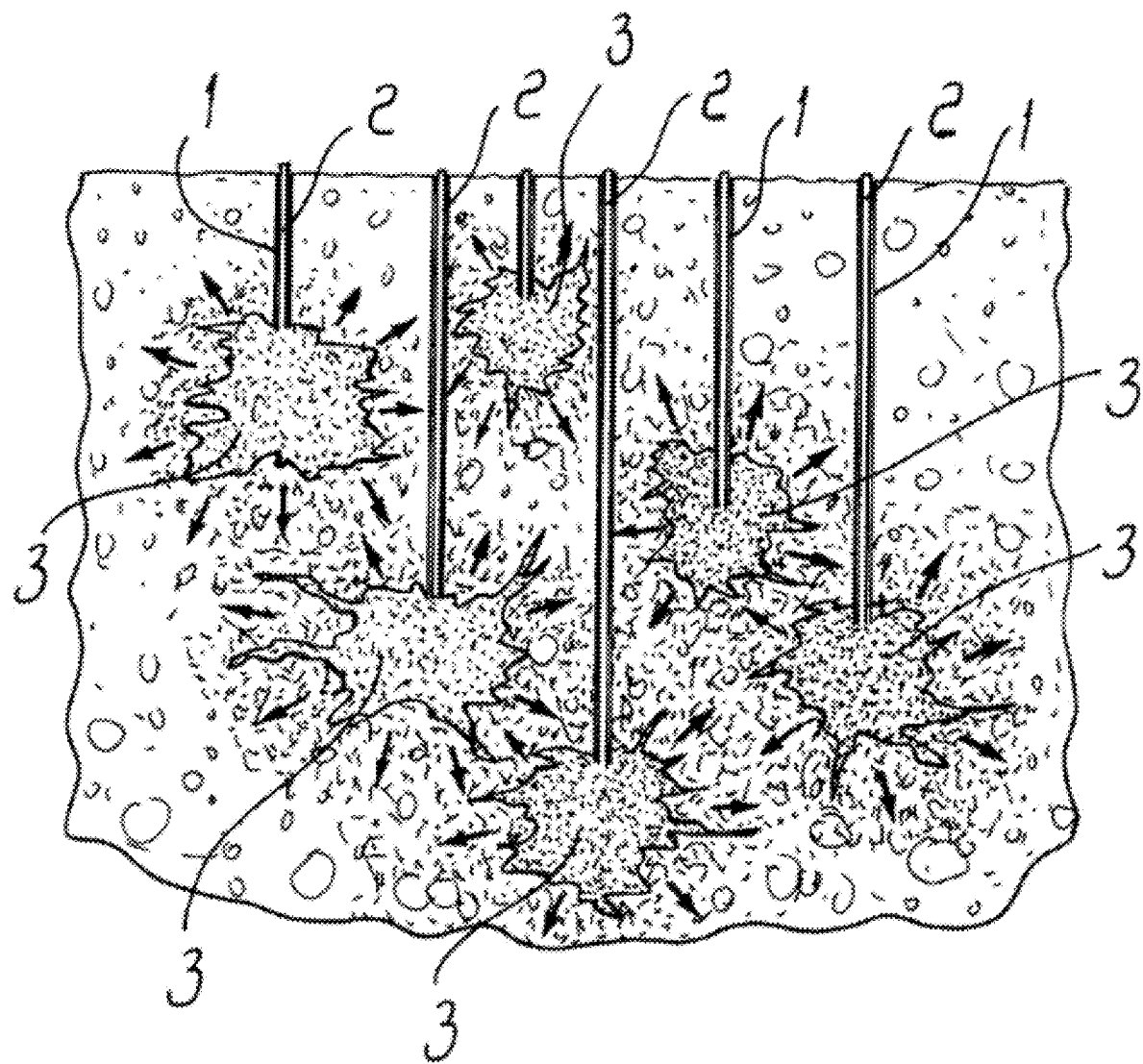
FIG. 4 is a view of the result of the expansion of the injected substance in the case of sequential injections performed with different tubes, inserted in different holes, in points spaced from each other and at different depths.

In some embodiments, the expandable substance can be injected through the holes 1 formed beforehand in the soil in a single injection step, as shown in FIGS. 1, 2, and 3, starting from the bottom, while the injection tube may be gradually retracted upwards, optionally with intermediate pauses, as shown in FIG. 2, so as to obtain different columns of hardened and expanded substance, or the substance can be injected, optionally by performing sequential injections at fixed and different depths in points which are three-dimensionally and uniformly spaced from each other so as to obtain regions of expanded and hardened substance within the foundation soil, as shown in particular in FIG. 4, according to requirements and according to the geological characteristics of the soil. In this last case, the tubes used for injection are left in the soil.

In some embodiments, once the substance 3 has been injected, since it has also penetrated in any voids and fractures of the soil thanks to its fluidity, expanding with great force and speed in all directions, it generates a force which compacts and compresses the soil all around, eliminating by compression or filling all voids and microvoids, even extremely small ones, expelling most of the water impregnating the soil, possibly agglomerating loose parts (granules and noncohesive parts) until a mass of soil is obtained which, throughout the treated layer, can no longer be compressed in relation to the weight that it has or will have to bear.

It should be noted that the expandable substance injected at different depths, in appropriately calculated points having a specific distance from each other, or along ascending lines, during expansion automatically flows towards the more compressible points, which as such offer less resistance to the expandable substance. In this manner, the regions which most need treating may be automatically treated more intensely, without leaving spaces with untreated regions.

In operation, the immediate nature of the expansion of the injected substance also allows to delimit the expansion region rather precisely, thus allowing to localize very well, in the intended points, the effect to be produced. The intense pressure applied by the injected substance to the surrounding soil is in fact due to the expansion caused by the chemical reaction and is not caused by hydraulic pressure. The expandable substance may be injected through a hydraulic pressure which, however, only has the purpose of introducing the substance in the chosen points.

In some embodiments, the immediate reaction of the injected substance, in terms of expansion and curing, prevents its migration to faraway areas, where a slow reacting substance may instead arrive. In fact, the slower the expansion reaction is the farther the substance arrives, to the detriment of the precise delimitation of the expansion effect and with consequent increase of the injection substance consumption.

Advantageously, since in the conditions of the invention the consolidation has a focused effect with low substance consumption, injection tubes may be used providing sufficient injection substance flow rates which have an inner diameter, for example of 10 mm, thus being easily insertable into and retractable from the soil. Tube diameters being smaller or larger by some millimeters are also usable.

To efficiently localize the effect of the consolidation, the injection may be carried out, with intermediate pauses. For example, injection periods of 15 seconds may be alternated with pauses of 1-2 seconds or even longer. The durations of the active injection and respectively of the alternating pause periods are in fact selectable to be the more suitable considering factors such as the injection depth, the injection substance composition, the length of the injection tubes, and the cross section of the injection tubes.

For obtaining a more rapid expansion reaction of the injected substance without having to switch to other compositions, where necessary, it is possible to raise by heating the temperature of the substance just before the injection operation.

As regards the hole depth, two different methods can be performed. A first method consists in treating the entire thickness of the soil layers which are compressible or have a low bearing capacity, so as to perform consolidation up to the solid horizon of the layers having a sufficient bearing capacity, regardless of their depth. The solid horizon can be detected by means of geotechnical research conducted on the soil. The second method instead consists in treating a layer of soil which, for reasons related to technical and/or economic convenience, does not reach down to the identified solid horizon, which might be located at an excessive depth, but is in any case thick enough to distribute the overlying weight over a wider surface. The layer of soil treated with the method according to the invention, by constituting a sufficiently compact, solid, and in any case light layer, can be effectively and broadly supported by the underlying layers of soil, even if those layers would not otherwise have a sufficient bearing capacity.

Until now, injection depth of up to 22 m have been successfully experimented, but with adapted tube cross-sections and accurately controlled substance injection flow rates, greater injection depths may be attained. The expansion of the injected substance following the chemical reaction of its components is very fast and develops a very high expansion force: up to 10,000 kPa or even higher.

Figure 5:
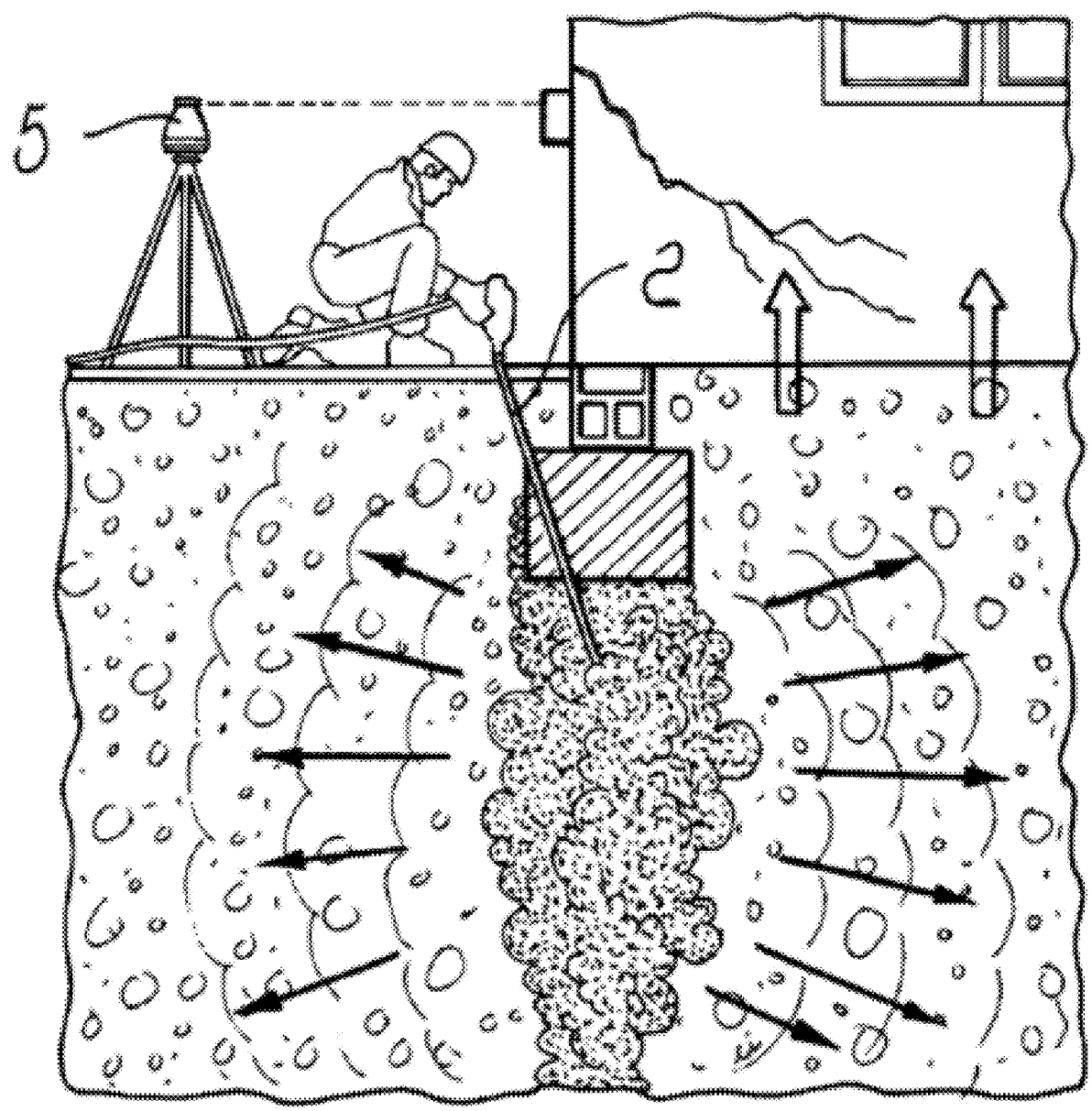
FIG. 5 is a schematic view of an injection operation, according to the invention, with constant monitoring of the sinking recovery of a building foundation.

During injection, the level of the overlying building or of the surface soil can be constantly monitored by means of a laser level 5 or another system (see FIG. 5). When the apparatus 5 indicates that the building or the soil surface begins to rise, this generally means that the compaction of the soil, in three dimensions all around the injection point, has reached very high levels which are generally higher than the required minimum values.

Through the constant monitoring operation, the precise moment when the soil begins rising at a precise spot, due to the narrowly focused expansion force, and further the exact amount of the lifting may be accurately detected and may be controlled in real time.

In some embodiments, the mass of injected substance, by reacting chemically, in fact expands with great force in all directions, and when the apparatus detects even a small rise at the surface, this means that the expandable substance has encountered less resistance in expanding in the vertical direction with respect to all other directions and that therefore the soil lying below and around the injected substance withstands and "rejects" all the weight (which is dynamic and therefore multiplied) not only of the entire mass of soil (and of any building) which rests statically thereon, but also of all the surrounding mass displaced (by friction and cohesion) at a load diffusion angle which is usually calculated at around 30° and is simply inverted. The raised soil, too, undergoes compression.

By repeating this operation at different depth levels (spaced by approximately 1 meter from each other, but variably according to the kind of soil and to the bearing capacity to be obtained), at each level, a greater bearing capacity is obtained than the required one. By acting in this last manner and by performing continuous injections along rising columns, wherein tree-like shapes are formed with a very irregular configuration, with protrusions, bumps, and projections even of considerable size produced by the different resistance of the soil to compaction and to the possible presence of interstices or fractures in the soil, in any case the entire mass and the treated layer of soil are compressed, packed and compacted; the water content decreases considerably; and the soil becomes a valid foundation soil adapted to stably support the building which lies above or is to be built.

The expandable substance can have a density varying indeed according to the resistance opposed by the surrounding soil to its expansion. In most cases, density can vary between 100 kg/m$^3$ and 800 kg/m$^3$. There may also be higher densities, since the density of the expanded substance is directly proportional to the resistance which it encounters to its expansion. The compression resistance of the expanded substance itself is a function of density.

A substance with a density of 100 kg/m$^3$ offers a resistance of approximately 14 kg/cm$^2$, whilst at a density of 300 kg/m$^3$ compression resistance is approximately 40 kg/cm$^2$. These values are far higher than those normally required for a foundation soil. In any case, where higher compression resistance values are required, even at different depths of the same soil, there is also a greater weight and therefore a higher resistance to expansion; accordingly, a denser and therefore stronger material forms automatically. In any case, it is possible to momentarily add weight to a soil surface or to a building.

In practice, the injected and hardened expanded substance does not support the overlying building on its own, though helping to achieve this purpose; the weight of the building is effectively supported by the foundation soil treated with the method according to the invention.

In practice it has been observed that the method according to the invention fully achieves the intended aim and objects, since it allows, in a very simple, rapid, effective, and final manner, to increase the bearing capacity of foundation soils until they fully comply to the desired capacity.

Typically, in what seems to be a general trend in ground consolidation techniques, see for example the document DE-A-33 32 256, a very rapid expansion, with very high expansion coefficients, creating rapidly increasing pressures in the treated soil, is purposely avoided, since it was shown to provoke unwanted, mainly vertical, fissures in the treated mass ground.

In the conditions of the invention, however, it has surprisingly been noted that fissures occurring between soil masses, not only do not affect the soil compaction, but can in fact be advantageously exploited.

Technical tests and studies, carried out on built lots where the consolidation method of the invention has been used, have demonstrated that the expansion of the injected material occurs first in directions where the soil offers less resistance, but only for a limited extent. In the case of a built spot this happens, in the first place, laterally to the foundation and not in the vertical direction, where the weight of the building acts.

Only after the ground compaction degree is such as to provide a resistance to the lateral expansion forces well exceeding the weight force exerted by the building, a vertical force is obtained such as to raise the foundation and the building. In fact, it is not only the weight of the building which has to be compensated for, but also other resistant forces, such as part of the weight of adjacent constructions, lateral friction forces and the flexural strength of the built structure itself.

Figure 9:
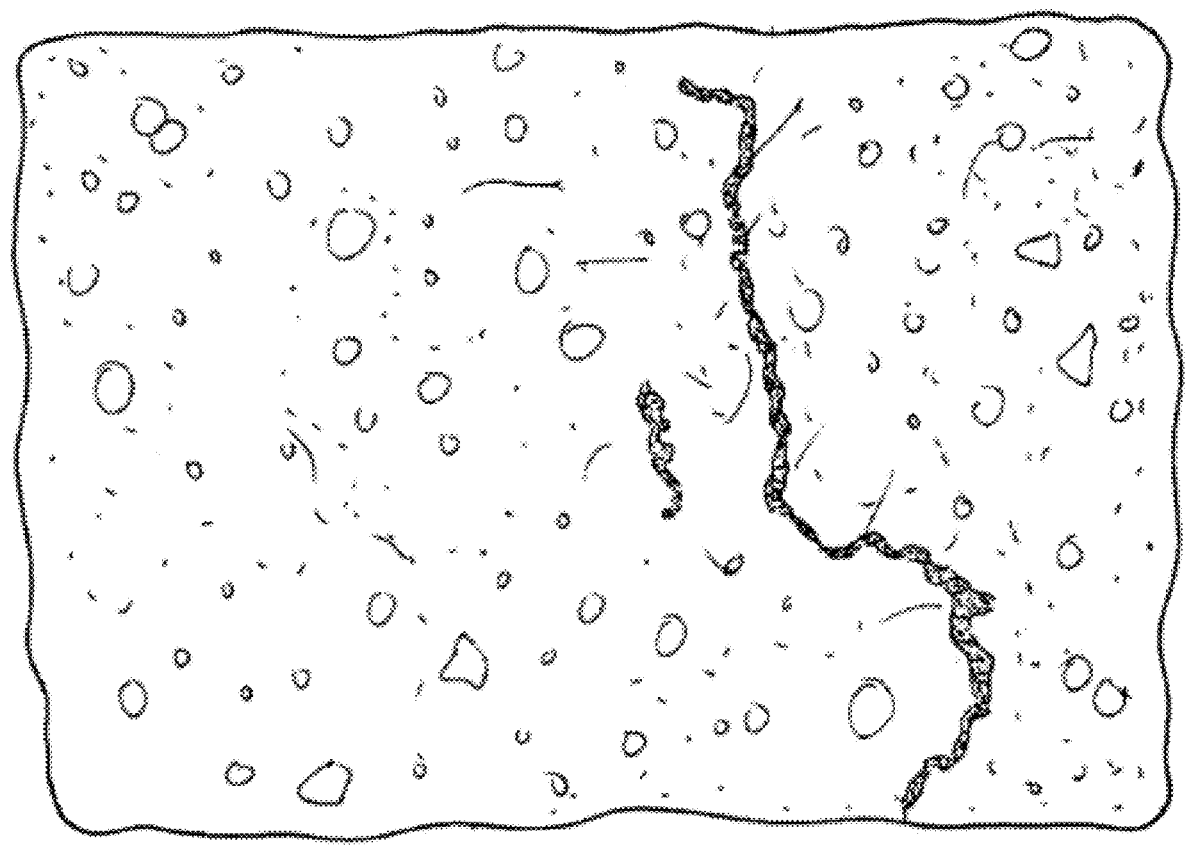
FIG. 9 is a sectional view of a soil area treated in accordance with the invention.

While an immediate reaction of the injected material, in terms of expansion and solidification, may provoke indeed fissures between soil masses forced to move with respect to each other by rapidly increasing, strong forces, a certain quantity of the injected substance appears in fact to fill up the fissures so as to "weld" satisfactory the soil masses, at least in the area to be consolidated, which is immediately close to the injection site and under the foundation of the built structure. For exemplification see FIG. 9, where a "welded" fissure may clearly be seen.

Figure 6:
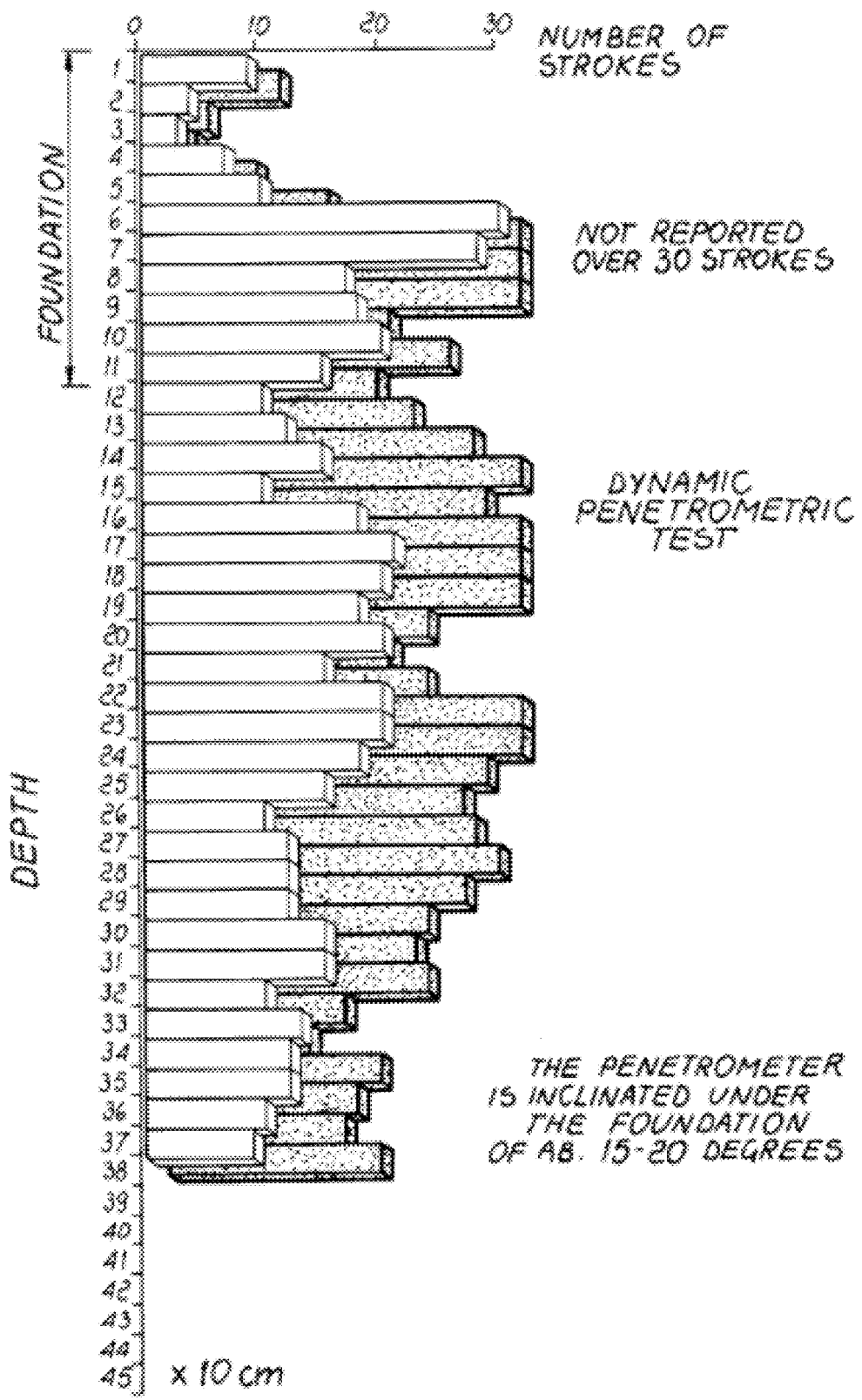
FIGS. 6-8 are comparative diagrams of dynamic penetrometric tests carried out on a soil area treated according to the invention.
Figure 7:
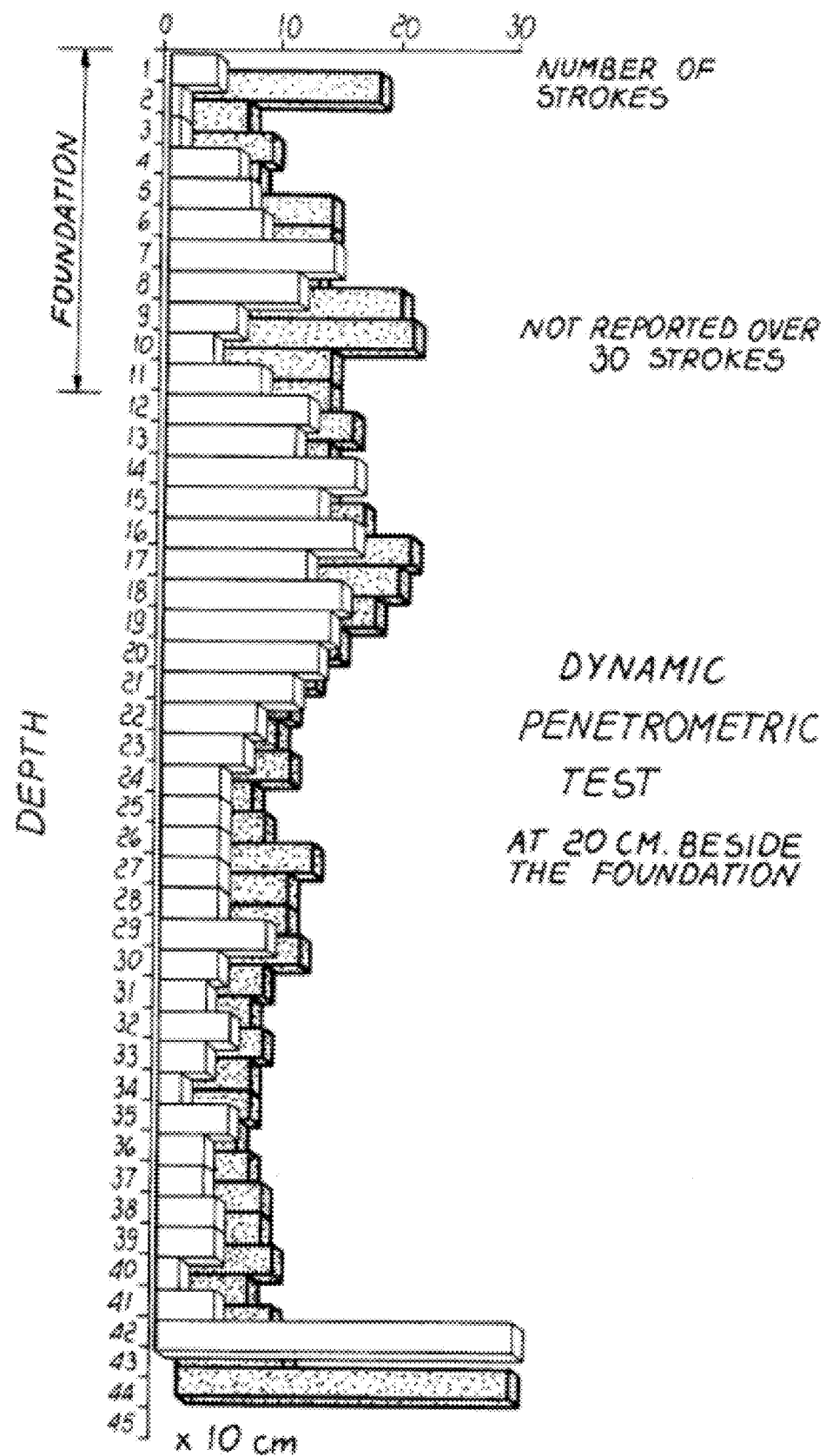
Figure 8:
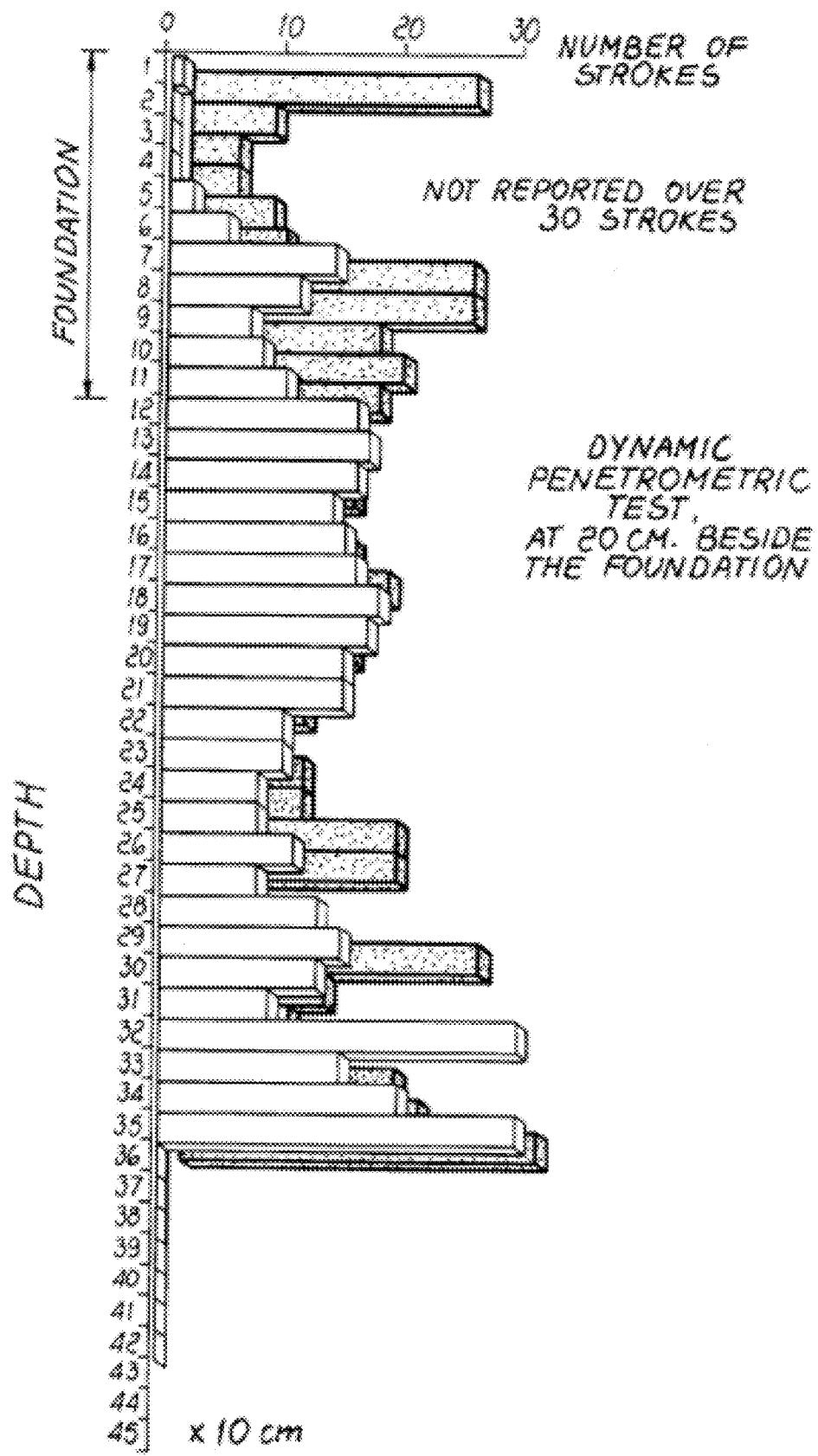

Penetrometric tests, the results whereof are shown in the diagrams of FIGS. 6-8, have been carried out both under built spots treated with the consolidation method according to the invention, after a soil lifting has been sensed by the level apparatus, and laterally thereto, in close vicinity, at about 20 cm from the foundation.

From these diagrams showing comparatively the soil bearing capacity before consolidation (the not shadowed prisms) and after the consolidation (the shadowed prisms), clearly appears that the main consolidation occurs under the foundation, between 120 and about 300 cm of depth (FIG. 6), while at only 20 cm laterally from the foundation, the consolidation appears, at the same depths as before, significantly diminished (FIG. 7).

It is believed that this clearly shows the focused effect of the consolidation carried out according to the invention which practically provides a noteworthy reinforcement of mainly the soil under the foundations.

The diagram of FIG. 8, drawn in the condition where an amount of expandable substance has been injected which has not provoked any detectable lifting reaction of the soil under the building foundation, shows that in fact, laterally, at only 20 cm from the foundation, practically no effective soil compaction has occurred which would have allowed generation of the vertical force necessary to the lifting and thereby also limiting the area where fissures may occur.

The method according to the invention has successfully been applied to consolidate the ground and to compensate subsidences under heavily loaded foundations in airports, such as those of the runaways, in industrial and commercial constructions such as those of roadways and equipment supporting slabs, as well as under very old, historic buildings and at archaeological sites.

A thorough review of treated sites have been made recently, and have all given satisfactory results. The inspections have been carried out in accordance with a procedure approved by the French Control Institute SOCOTEC consisting substantially in injecting, at a site selected by an inspector in a treated zone, at random, a small quantity of the injection substance (about 20% of the quantity initially injected). The result has been considered positive if the injection triggered at least a minimum lifting effect of the soil surface.

The method thus conceived is susceptible of numerous modifications and variations, all of which are within the scope of the inventive concept; all the details may furthermore be replaced with other technically equivalent elements. Reference will now be made in detail to the embodiments of the present disclosure, examples of which are illustrated in the accompanying drawings. The present disclosure may, however, be embodied in many different forms and should not be construed as being limited to the embodiments set forth herein. Rather, these embodiments are provided so that this disclosure will be thorough and complete, and will fully convey the concept of the disclosure to those skilled in the art.

Figure 10:
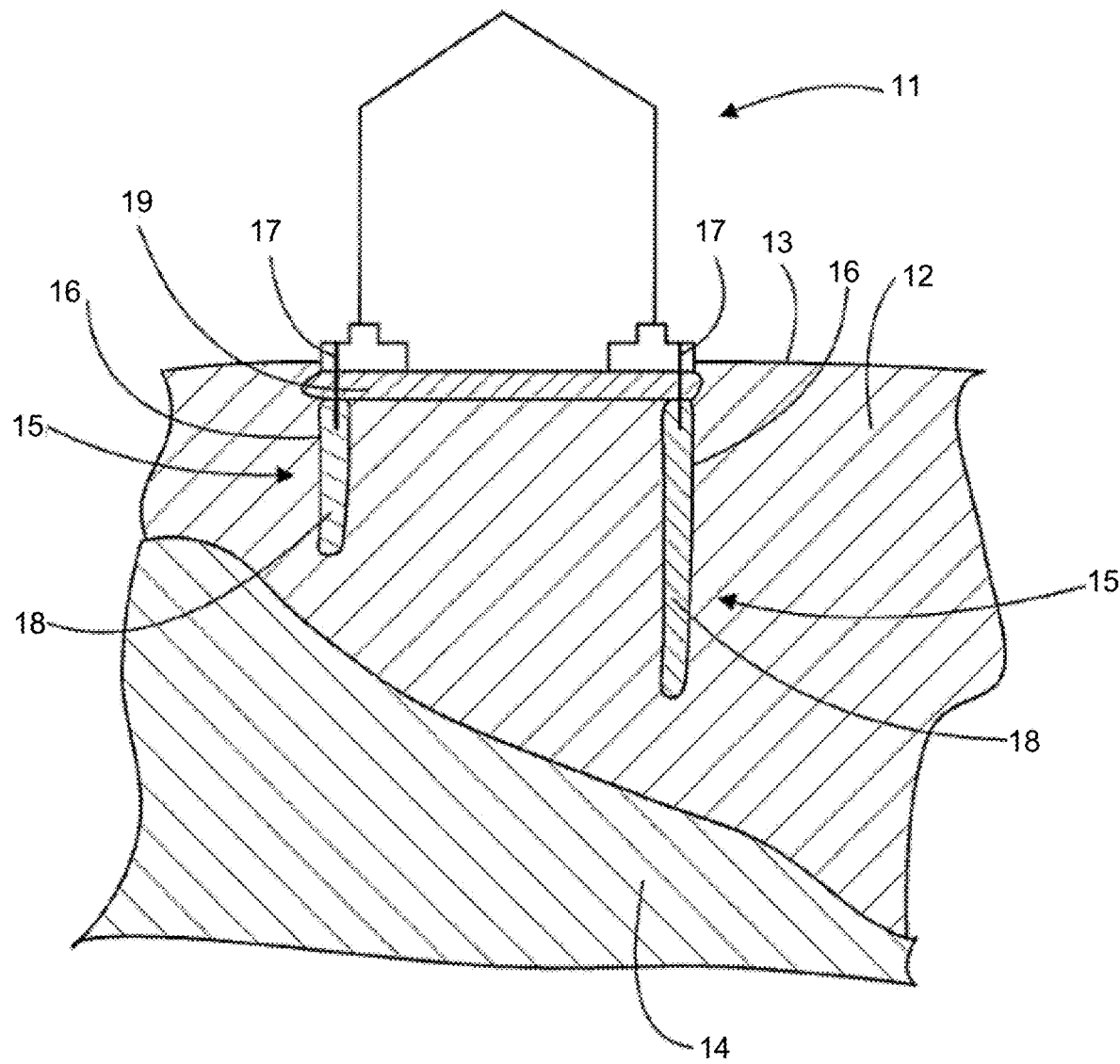
FIG. 10 shows schematically how a structure is supported by cohesion pillars.

Referring now to FIG. 10, an embodiment of an existing built environment shows building 11, which is arranged on a compressive ground 12. The compressive ground 12 may be clay, for instance. The distance from the ground surface 13 to a hard ground, such as rock 14, is so long that the building 11 rests on cohesion pillars 15.

In some embodiments, the cohesion pillar 15 may be formed by an expansion element 16, inside which there is injected polymer 18 along an injecting pipe 17. The polymer 18 is preferably such that, when reacted, it is elastic. Further, the polymer 18 is such that it absorbs water from the surrounding ground. Further, the polymer 18 is preferably porous such that it provides a so-called sponge effect, whereby it is able to absorb water effectively. As water is absorbed into the expansion element 16 from the surrounding ground, naturally a wall of the expansion element 16 is to be of water-permeable material. The wall of the expansion element is to be flexible, yet preferably substantially non-stretching material. A good material suitable for the purpose is a geotextile.

The polymer 18 is such that unreacted it is fluent, i.e. it can be injected unreacted along the injecting pipe 17 into the expansion element 16. The polymer 18 reacts in the expansion element 16. The reaction of the polymer 18, i.e. its chemical reaction comprises at least solidification and/or hardening thereof.

Further preferably, the chemical reaction of the polymer is arranged to produce heat. In that case, said chemical reaction enables the ground 12 surrounding the expansion element 16 to be dried.

The cohesion pillar 15 may be secured to the structure to be supported through the injection pipe 17. On the other hand, instead of or in addition to the injecting pipe 17, the expansion element 16 may be connected directly to the structure to be supported.

When the polymer 18 is injected, the injecting pipe 17 may be first arranged at the bottom of the expansion element 16, and in the course of injection, the injecting pipe may be drawn upwardly, and finally, the injecting pipe 17 may be drawn out altogether, if so desired, from the inside of the expansion element 16. Thus, in this case the expansion element 16 and the polymer 18 therein constitute the cohesion pillar 15, without any other structures.

The cohesion pillar 15 is thus formed preferably such that first is expanded the lower part of the expansion element 16. Only thereafter the polymer 18 is injected such that the expansion element 16 is filled up from bottom upwards. The expanded portion of the lower part of the expansion element 16 anchors the cohesion pillar in the ground, which enables the injecting pipe 17 being drawn upwardly without the expansion element 16 substantially rising upwardly in the ground. This solution disturbs the ground surface and superficial parts as little as possible.

The structure to be supported may thus be an existing structure, such as building 11, through the foundation of which there is provided a hole, through which are arranged the expansion element 16 and the injecting pipe 17. The solution disclosed here is particularly well suited for supporting ground-supported structures. The polymer 18 is injected through the injecting pipe and it does not react until in the expansion element 16. Consequently, the cohesion pillar 15 may be provided relatively easily to support the existing structures. FIG. 10 also shows a gravel bed 19 beneath building 11.

In the embodiment of FIG. 10 the distance from the ground surface 13 to the rock 14 varies such that on one side of building 11 there is compressive ground 12 between building 11 and the rock 14 less than on the other side. In this type of example, the cohesion pillar 15 may be arranged to compensate for the subsidence of building 11 either on one side of the building only, or such that on one side the expansion element is longer than on the other side, as is shown in FIG. 10. Thus, is prevented uneven subsidence, i.e. inclination, of the structure.

The outer diameter of the injecting pipe 17 may vary between 5 and 100 mm, whereby its inner diameter varies, for instance, between 4 and 95 mm, respectively. An example of the injecting pipe 17 is a steel pipe having an inner diameter of 12 mm. The length of the injecting pipe may vary between 1 and 20 m, for example. The injecting pipe 17 may be made of metal, such as steel, or it may also be made of some other material, such as plastic, e.g. polyethylene PE. Also, the injecting pipe 17 need not necessarily be rigid. The injecting pipe 17 may thus be a plastic hose or pipe, for example. If the injecting pipe 17 is a hose, its wall may be provided with textile reinforcement fabrics or metal or other similar reinforcements.

In some embodiments, the wall of the expansion element 16 is thus of water permeable and possibly substantially non-stretching material, such as geotextile. It is also possible to use some other flexible and durable material. As the material of the expansion element 16 it is possible to use a plastic, such as polyester or polypropylene, or artificial fiber or natural fiber. In some embodiments, the wall of the expansion element may be inelastic. The wall of the expansion element may also include metallic reinforcement material or glass fiber, or some other suitable reinforcement material. The expansion element may be provided either with seams or without seams. The seam may be made, for instance, by sewing, gluing, using an attachment element, riveting, welding, soldering, melting, or by some other mechanical, chemical, thermal or electrotechnical method or a combination thereof.

In some embodiments, the wall thickness in the expansion element 16 may vary between 0.05 mm and 5 mm, for example, depending on the material, size of the expansion element, expansion pressure, etc.

Before fitting the injecting pipe 17 inside the ground the expansion element 16 is wrapped or folded against the injecting pipe 17. When the expansion element 16 is full of reacted polymer 18, its outer diameter may vary between 15 cm and 1 m, for instance. Correspondingly, the length of the expansion element 16 may vary between 20 cm and 20 m, for instance. When the maximum outer diameter of the expansion element 16 is 40 cm, for instance, it can be wrapped or folded around the injecting pipe 17 such that their outer diameter is less than 40 mm, whereby the mounting of the injecting pipe 17 and the expansion element 16 in the ground is simple and easy.

In some embodiments, the expansion element 16 may be, for example, cylindrical when it is full of polymer 18. Further, the expansion element may be slimmer at the upper and lower ends, and the middle portion may be larger in diameter. The external form of the expansion element prior to injecting the polymer inside the expansion element 16 is irrelevant. After the polymer has reacted inside the expansion element, the expansion element 16 achieves its final shape, which is affected, in addition to the properties and the amount of the polymer 18, by the properties of the ground surrounding the expansion element.

How much water is absorbed, may be determined on the basis of the shearing strength of the ground 12. Typically, it is thus assumed that the lower the shearing strength of the ground, the higher its water content. The lower the shearing strength, the more the polymer is arranged to absorb water. It may be given as exemplary values that if the shearing strength of the ground 12 is e.g. less than 20 kPa, the polymer 18 is arranged to absorb water to the extent that its total mass will increase by at least 10% and if the shearing strength is e.g. less than 5 kPa, the increase in the total mass is arranged to be at least 50%.

The polymer 18, when reacted, may be elastic. Resilience may thus be elastic, e.g., recoverable, or resilience may be creep, e.g., irrecoverable. Elasticity of the cohesion pillar, i.e. the elasticity of the polymer 18 after solidification and/or hardening, may be presented as a modulus of elasticity, the magnitude of which may be 15 to 500 MPa, for instance. Preferably the modulus of elasticity is less than 300 MPa. The desired value of the elasticity of the cohesion pillar polymer 18 may be determined on the basis of the compressibility of the ground.

If the material has a low free expansion density, i.e. its density is low, its elasticity is typically low. The elasticity of the polymer may be affected, for instance, by the amount of water absorbed. So, the elasticity of two different cohesion pillars, for instance, may be different, even though their dimensions and the polymer injected therein, and the amount thereof, are identical, but the grounds, where the cohesion pillars are located, are different in moisture content.

The polymer 18 may be, for example, a mixture mainly consisting of two components. In such a case, the first component may mainly contain polyether polyol and/or polyester polyol, for example. The second component may contain isocyanate, for instance. The volumetric ratios of the first component to the second component may vary between 0.8 to 1.2:0.8 to 1.8, for example. The polymer may further contain catalysts and water and, if desired, also other components, such as silica, rock dust, fiber reinforcements, and other possible additional and/or auxiliary agents. The use of a single-component polymer is also possible in connection with the solutions disclosed in this description.

The polymer 18 may be non-expanding, in which case its chemical reaction in the expansion element 16 typically comprises solidification and/or hardening. The polymer 18 may also be material expanding as a result of a chemical reaction, whereby the polymer 18, when reacting, expands in the expansion element 16 and, in addition to expansion, also solidifies and/or hardens as well. The polymer 18 may be arranged to expand, for instance, 1.5 to 20 times from the original volume. The material expanding as a result of a chemical reaction need not be fed into the expansion element 16 at so high hydraulic pressure as a non-expanding polymer. Thus, the polymer feeding equipment may be provided simpler.

The capacity of the polymer to absorb water is affected, inter alia, by a gelling time of the polymer. So, if the polymer is desired to absorb more water, the gelling time is to be increased, for instance. It may be given as exemplary values that if in a clay ground having a shearing strength of 10 kPa, water absorption, i.e. increase in polymer total mass with water absorption, is desired to be over 50%, the gelling time is to be controlled to a value of 40 sec, for instance. When using the above-mentioned two-component substance, the water absorption may be affected by the mixture ratio of the first to the second component. If in said polymer the volumetric ratio of the first to the second component is, for instance, 1:1.25, the polymer absorbs more water than in a situation, in which the volumetric ratio of the first to the second component is 1:1.

The elasticity of the polymer 18 may be controlled by changing its density, for instance. The elasticity is thus also affected by the water content in the polymeric mixture. Thus, the desired elasticity is determined, for instance, by adjusting the amount of a foam-producing auxiliary agent or by controlling the amount of the polymer to be injected in the expansion element of a specific volumetric capacity.

The structure, for the supporting of which the above described cohesion pillar 15 is employed, may thus be a ground-supported building as illustrated in FIG. 10. Further, the structure to be supported may be such that is partly pile-supported and partly ground-supported, for instance, such that the foundation is piled and the slab of the building is ground-supported. Further, the structure to be supported may be an earth bank or a road on a cohesion ground, or another similar structure to be supported.

Referring now to FIGS. 11-21 embodiments of a construction process in accordance with the present disclosure are provided. Embodiments included herein may provide a process 10 for real-time displacement control using expansive grouts. Accordingly, embodiments of the present disclosure may relate to a method of using expansive grouts injected into the ground to protect the existing built environment (e.g., domestic, commercial and military, buildings, pavements, utility services, tunnels, railways, airports, water supply and water treatment facilities, manufacturing and process plants, power plants, storage facilities, etc.) from the damaging effects of ground movements.

Embodiments of the present disclosure may provide a method or process 10 capable of protecting the existing built environment from becoming damaged or unserviceable as a result of ground displacements predicted to occur due to some phenomenon or activity.

Accordingly, embodiments included herein may rely upon the ability to predict, within tolerable accuracy, the magnitude of the ground movements that will occur as a result of the phenomenon. A scheme may then be designed to enable the expansive grouts to be injected in "Real-Time" to prevent or mitigate the impact of these movements on the existing built environment. The phrase "real-time", as used herein, may refer to activity that may be concurrent with the phenomenon causing the ground movement. This may be concurrent and continuous and/or may be concurrent and intermittent. As a minimum, this would be a single program of injections. In most cases, however, it is probable that multiple injection phases may be required.

Some examples of activities or phenomenon that may cause such ground displacement are many and varied and may include, but are not limited to, construction activities, mining, change in groundwater levels, subsidence, climatic change, flooding, etc. The construction activities that are most likely to cause movement are tunneling, shaft sinking, basement construction, earthworks, etc. However, these are provided merely by way of example as numerous activities could create such a situation.

In some embodiments, the processes described herein may provide a method of compensating for ground displacements between the source of the movement and the asset or entity to be protected by the injection of an expansive grout. The location of the grout injection(s) may be dependent upon many factors and may be decided as part of the scheme design that may precede the injection phase. The optimum injection point may be close to the source of the movement or close to the entity to be protected or somewhere in between. Due to access restrictions at the surface or in the ground it may not be possible to select the optimum grout injection position. In these circumstances, the scheme may need to be designed taking into considerations these practical constraints.

In the case of new tunnel construction, in certain circumstances it may be desirable to drill the injection holes from the tunnel itself. These injection holes would then be accessed for injection from within the tunnel.

In the case of a single tunnel the injection holes may be drilled vertically and/or sub vertically and/or inclined forwards.

In the case of multiple tunnel construction, the first tunnel may also be used to provide access to install the injection arrays for the second and subsequent tunnels; junctions, cross passages etc.

As process 10 can be effectively operated with small scale plant and equipment, in some circumstances direct intervention from the asset to be protected may be desirable, e.g. from within a building or from within a tunnel.

As discussed above, expansive grouts may create a large displacement force that may be capable of dilating the ground. Grout formulations and injection strategies may be selected for the prevailing conditions and to create the desired magnitude and orientation of movement. Different grout formulations and injection strategies may be selected depending upon the ground type and the nature of the ground displacements to be compensated for.

Embodiments included herein may provide a method of ground improvement. This ground improvement may be required to improve the strength and/or the stiffness of the ground and/or reduce the mass permeability of the ground for groundwater or ground gas control purposes.

In some embodiments a phased approach may be employed that may first utilize the injected grouts to improve the ground and then in subsequent phases the grout may react against the improved ground to create ground displacement.

Embodiments included herein may provide a long-term durable and stable solution commensurate with the societal design life expectations and with that of the assets it protects. Grout selection may also take into account the environment so as not to create any adverse impacts on the environs of its use.

In some embodiments, the process may be carefully monitored and controlled using accurate surface and sub-surface instrumentation. Injection campaigns may be planned as part of the pre-commencement design and movements associated with each injection may be compared with the design predictions. A holistic approach to the monitoring and the grouting may be required and feedback loops to the designer and to the grout teams ensure precise displacement control at all times.

In some embodiments, boreholes of various configurations may be used without departing from the scope of the present disclosure. For example, in some embodiments inclined injection boreholes may be used to protect the existing assets. In this scenario drilling of the injection pipes may be assumed to be undertaken from within the construction worksite required for the construction of the new shaft. In some embodiments, horizontal boreholes may be used. Accordingly, a top array may be injected with grout to stabilize and strengthen the ground. A lower array may be used to inject the grout which may create the ground displacements. The top array may be grouted in advance of the lower array. The arrays could also be installed in a sub-horizontal configuration if required. However, it should be noted that any suitable combination and/or arrangement of boreholes may be used in accordance with the present disclosure.

Figure 11:
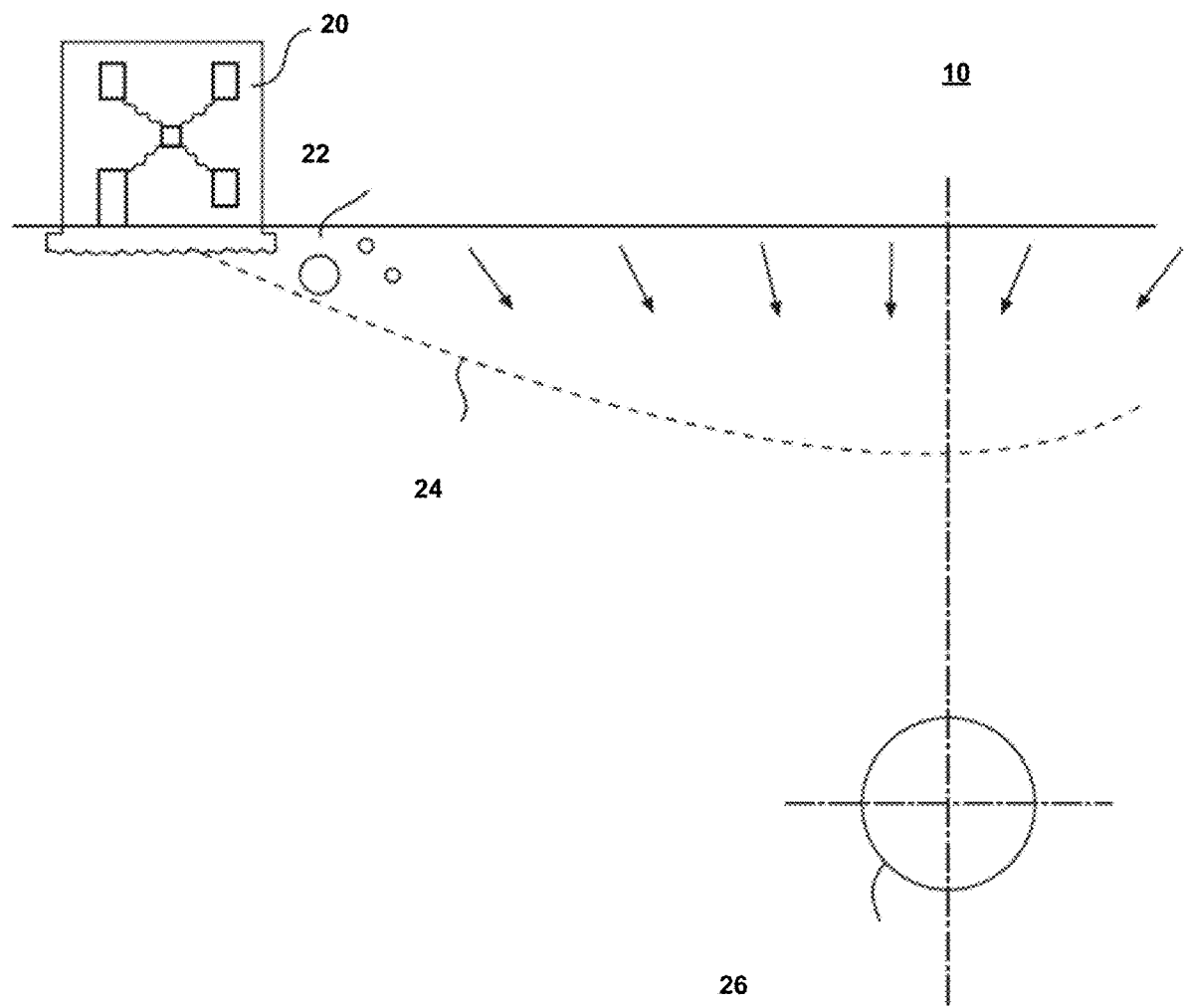
FIG. 11 is a schematic depicting an example showing the effect of ground movement caused by the construction of a new tunnel on the existing built environment without applying the beneficial effects of real-time displacement control.
Figure 12:
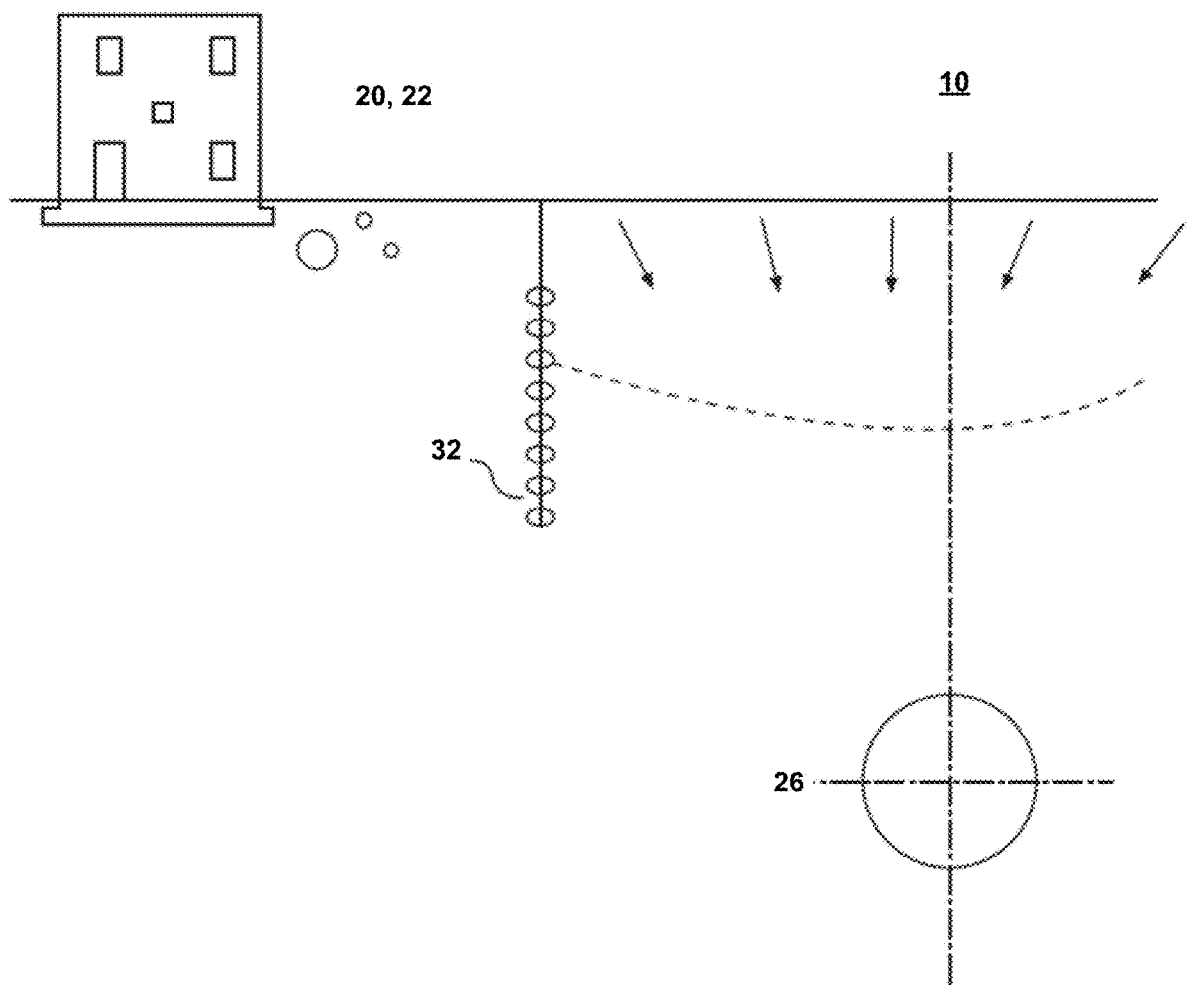
FIG. 12 is a schematic depicting an example showing how the existing built environment is protected from the effect of ground movement caused by the construction of a new tunnel in accordance with an embodiment of the present disclosure.

Referring now to FIGS. 11-21, examples consistent with embodiments of the present disclosure are provided. FIGS. 11-12 show diagrams of an existing built environment including existing building 20, which may have been damaged by settlement, and existing utilities 22, which also may have been damaged by settlement, that may be protected using the teachings of the present disclosure. FIGS. 11 and 12 show the effect of ground movement caused by the construction of new tunnel 26 on the existing built environment. In FIG. 11 process 10 for real-time displacement control using expansive grouts protection is not applied and the displacements caused by tunneling cause settlement and rotation of the building and services resulting in damage and/or loss of functionality or service, which is exemplified by profile of ground displacement 24 (scale exaggerated). FIG. 12 shows the same scenario but with the process 10 for real-time displacement control using expansive grouts (i.e. injection borehole(s) 32) being applied between the source of the movement (new tunnel 26) and the assets to be protected (existing building 20 and existing utilities 22).

Figure 13:
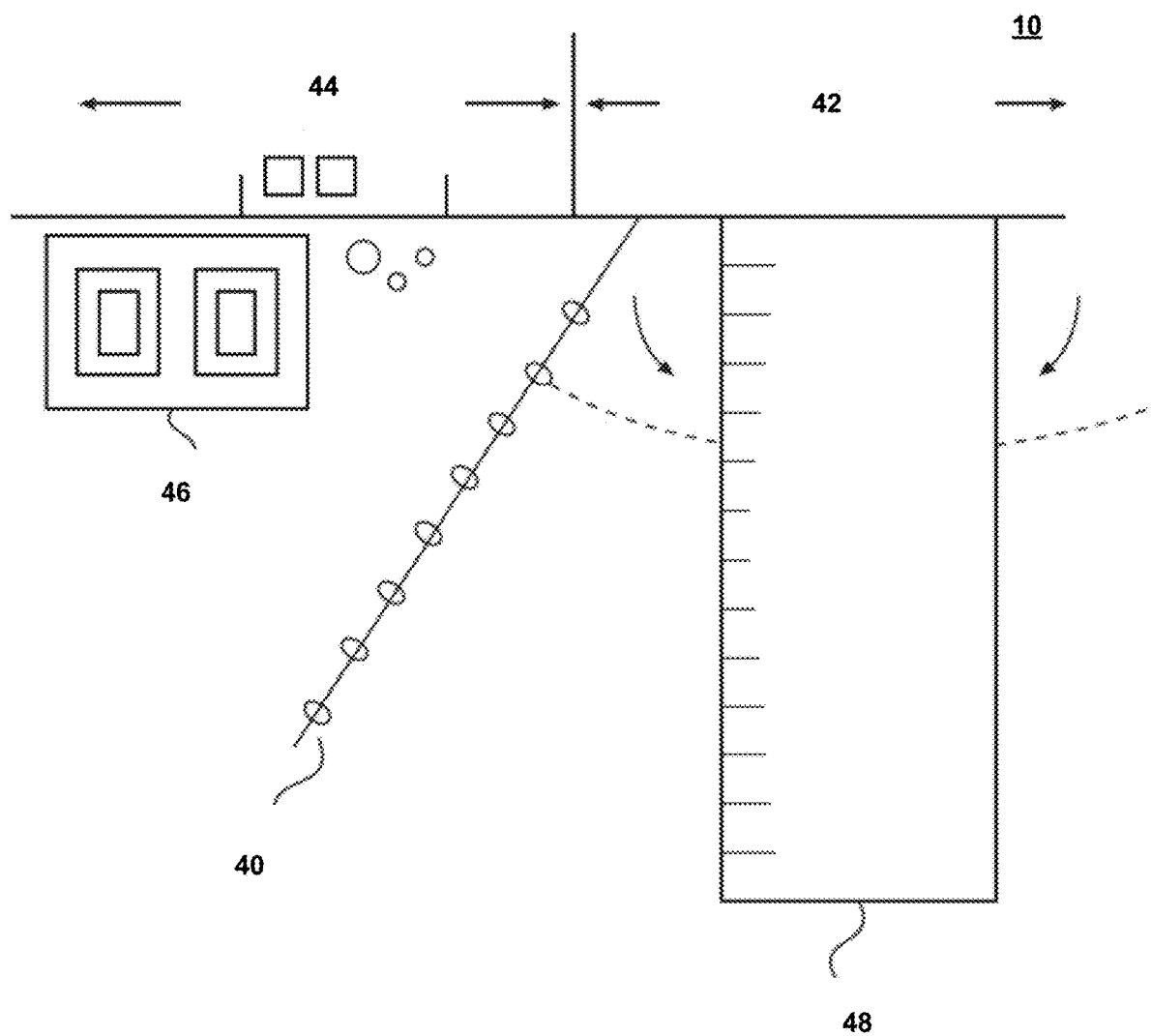
FIG. 13 is a schematic depicting an example showing use of inclined injection boreholes to protect the existing assets in accordance with an embodiment of the present disclosure.

FIG. 13 shows the use of process 10 for real-time displacement control using expansive grouts via inclined injection boreholes 40 to project the existing assets, which includes existing sub-surface tube tunnel 46. In this example drilling of the injection pipes is assumed to be undertaken from within construction worksite 42, which includes no surface access road 44, required for the construction of new shaft 48.

Figure 14:
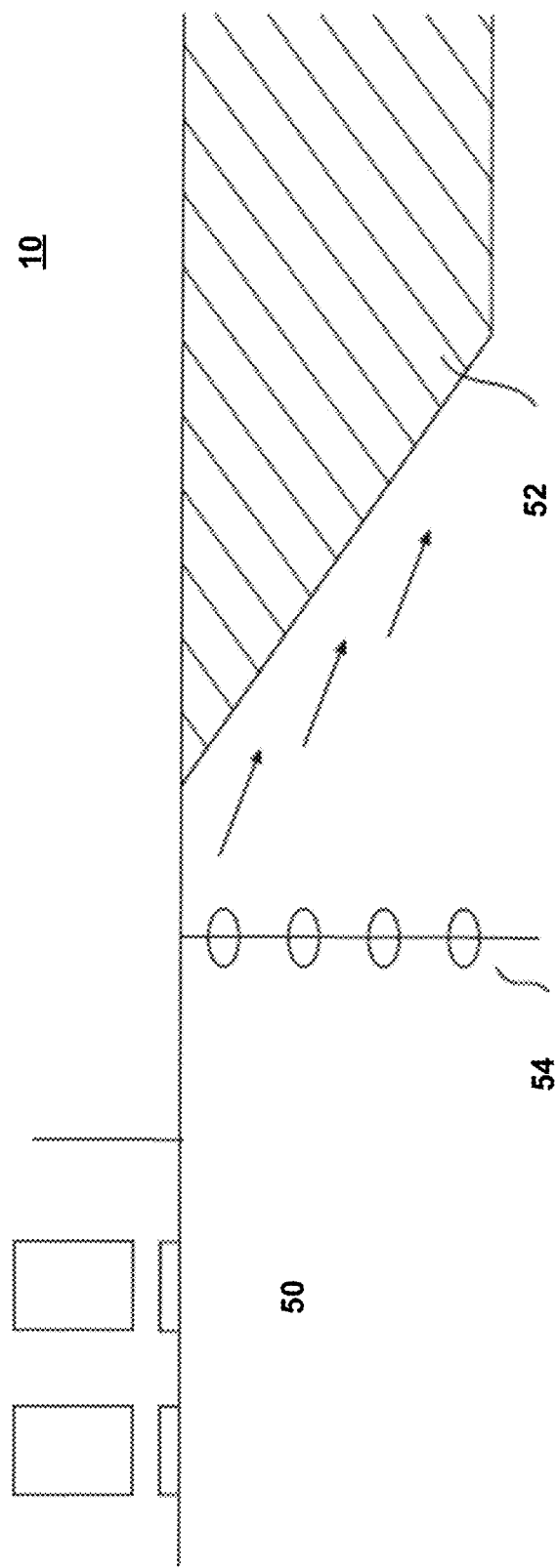
FIG. 14 is a schematic depicting an example of an existing railway line being isolated from the movements induced by the excavation of a nearby road cutting by injection boreholes drilled vertically from the surface in accordance with an embodiment of the present disclosure.

FIG. 14. shows existing railway line 50 (hereinafter "existing railway 50") being isolated from the movements induced by the excavation of nearby road cutting 52 by process 10 for real-time displacement control using expansive grouts introduced via injection boreholes 54 drilled vertically from the surface.

Figure 15:
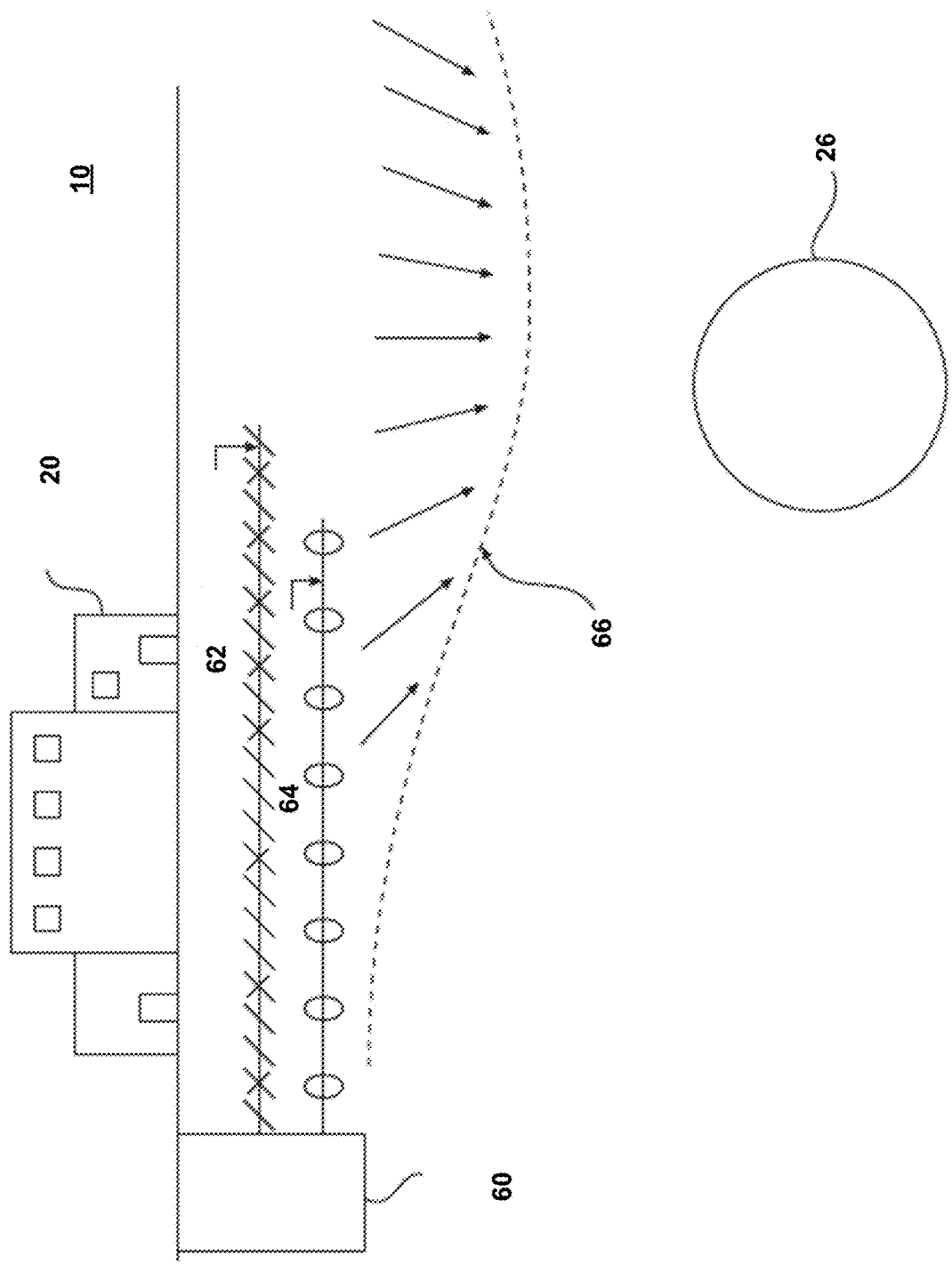
FIG. 15 is a schematic depicting an example showing the use of horizontal boreholes in accordance with an embodiment of the present disclosure. In this example a two-stage approach is applied; the first stage utilizes a ground improvement array to strengthen and stiffen the ground; in the second stage the displacement control array is injected to compensate for movements caused by the construction of a new tunnel.

FIG. 15 shows the use of process 10 for real-time displacement control using expansive grouts introduced via horizontal boreholes drilled from temporary grouting access shaft 60 constructed specifically for this purpose. Uppermost improvement array 62 is injected with slow setting grout to stabilize and strengthen the ground. Lower displacement control array 64 is used to inject a fast setting grout which will create the ground displacements necessary to compensate for the movements caused by the construction of new tunnel 26. Uppermost array 62 is installed in advance of the lower array. The arrays could also be installed in a sub-horizontal configuration if required or by directional drilling from the surface. The ground displacement caused by process 10 for real-time displacement control using expansive grouts in this example is exemplified by profile of ground displacement 66 (scale exaggerated).

Figure 16:
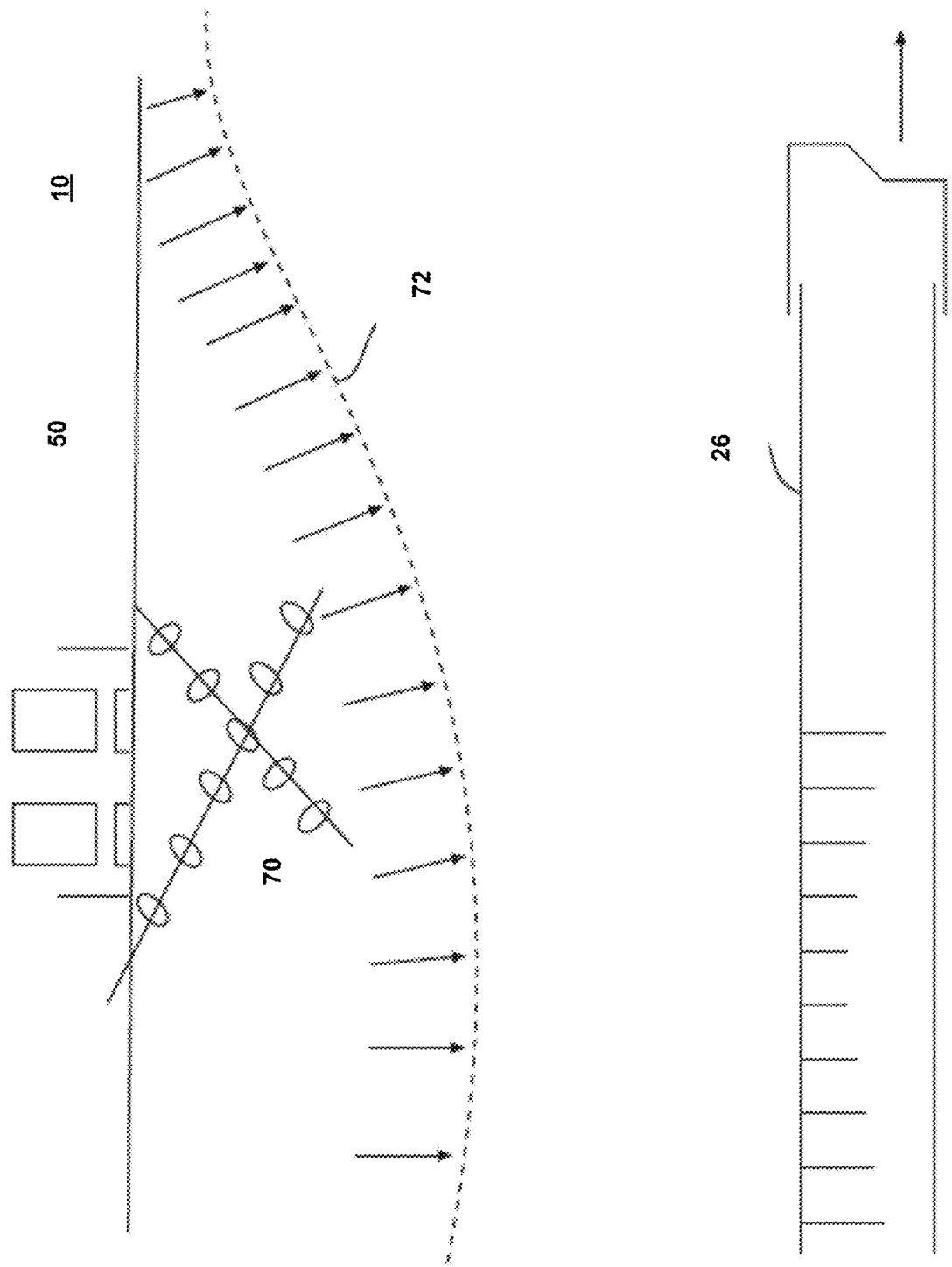
FIG. 16 is a schematic depicting an example of a vertical section showing a new tunnel being constructed beneath an existing railway in accordance with an embodiment of the present disclosure.

FIG. 16 shows new tunnel 26 being constructed beneath existing railway 50. In this example, process 10 for real-time displacement control using expansive grouts is introduced via injection boreholes 70 which are drilled in an inclined array from both sides of existing railway 50. Alternatively, they could be constructed using directional drilling techniques. The ground displacement caused by process 10 for real-time displacement control using expansive grouts in this example is exemplified by profile of ground displacement 72.

Figure 17:
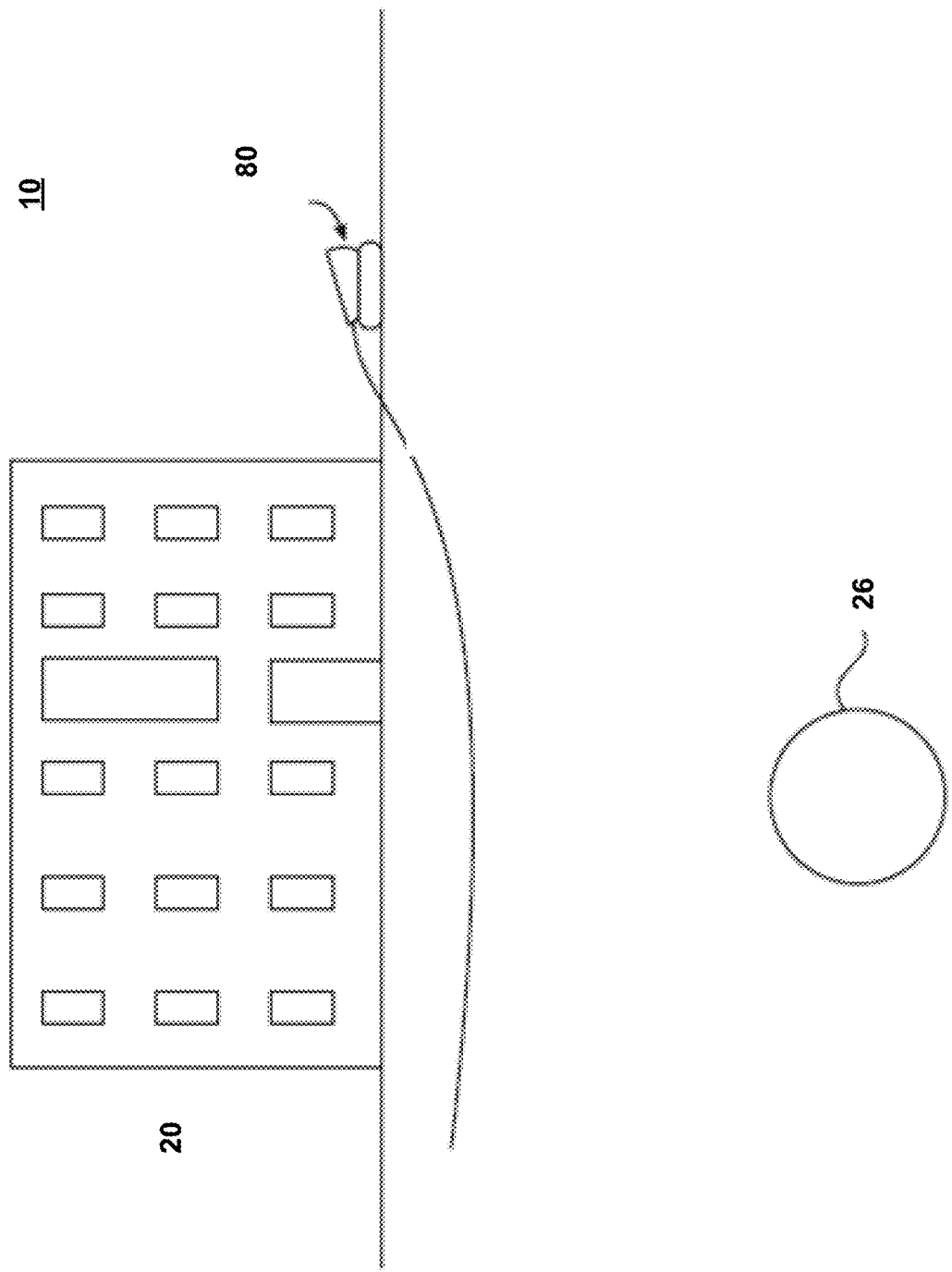
FIG. 17 is a schematic depicting an example of a new tunnel being constructed beneath an existing building in accordance with an embodiment of the present disclosure. In this example the injection boreholes are installed using directional drilling techniques from the surface.

FIG. 17 shows new tunnel 26 being constructed beneath existing building 20. In this example, process 10 for real-time displacement control using expansive grouts is introduced via injection boreholes which are constructed using directional drilling techniques, which includes bidirectional drill 80. In this embodiment, injection tubes may be installed under the building using directional drilling techniques.

Figure 18:
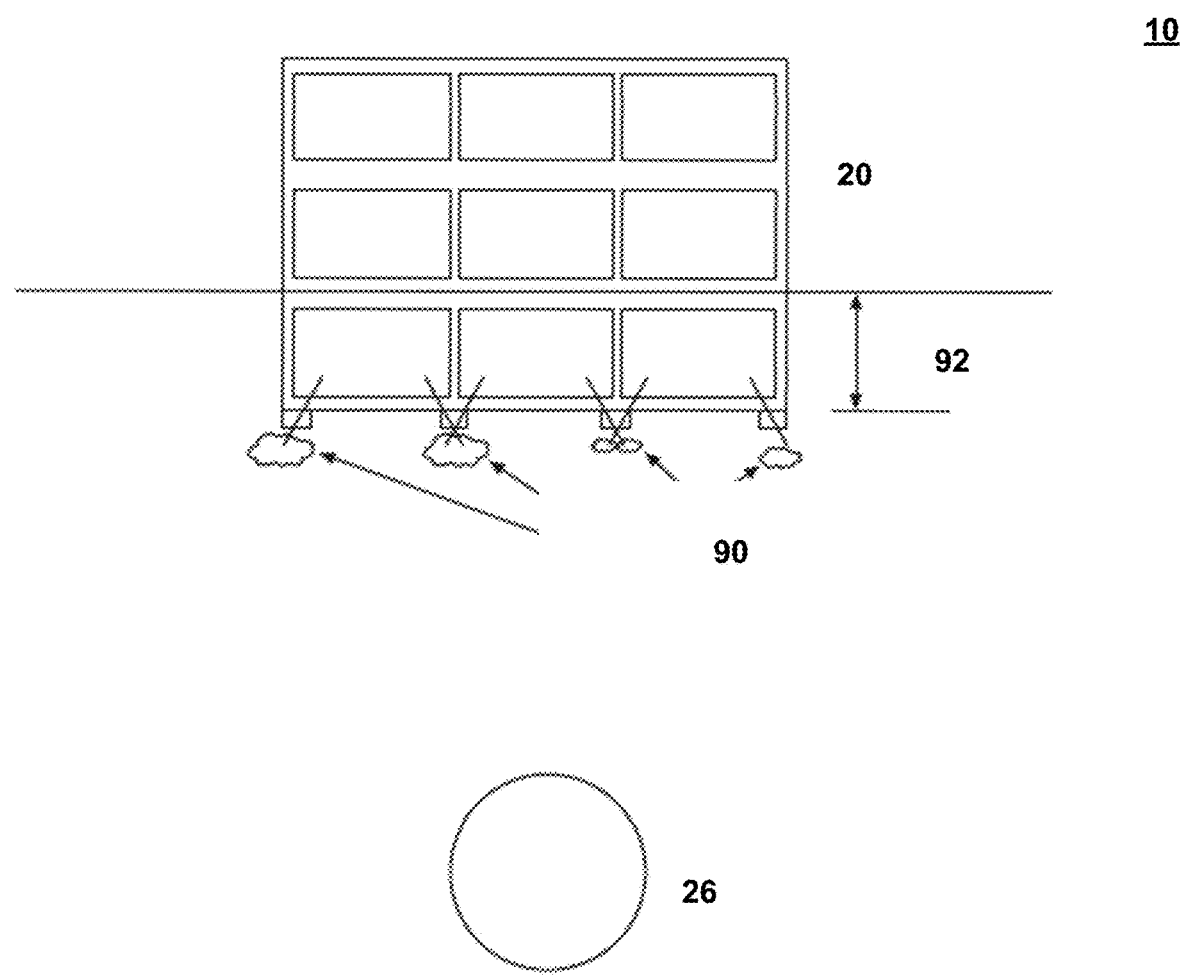
FIG. 18 is a schematic depicting an example of a new tunnel being constructed beneath an existing building where the process allows for real-time direct intervention from the asset to be protected (e.g., from within a building or within a tunnel) in accordance with an embodiment of the present disclosure.

FIG. 18 shows new tunnel 26 being constructed beneath existing building 20. In this example, process 10 for real-time displacement control using expansive grouts is introduced via injection boreholes 90 which are drilled from basement 92 of existing building 20. For buildings without a basement drilling would be undertaken from the ground floor slab level.

Figure 19:
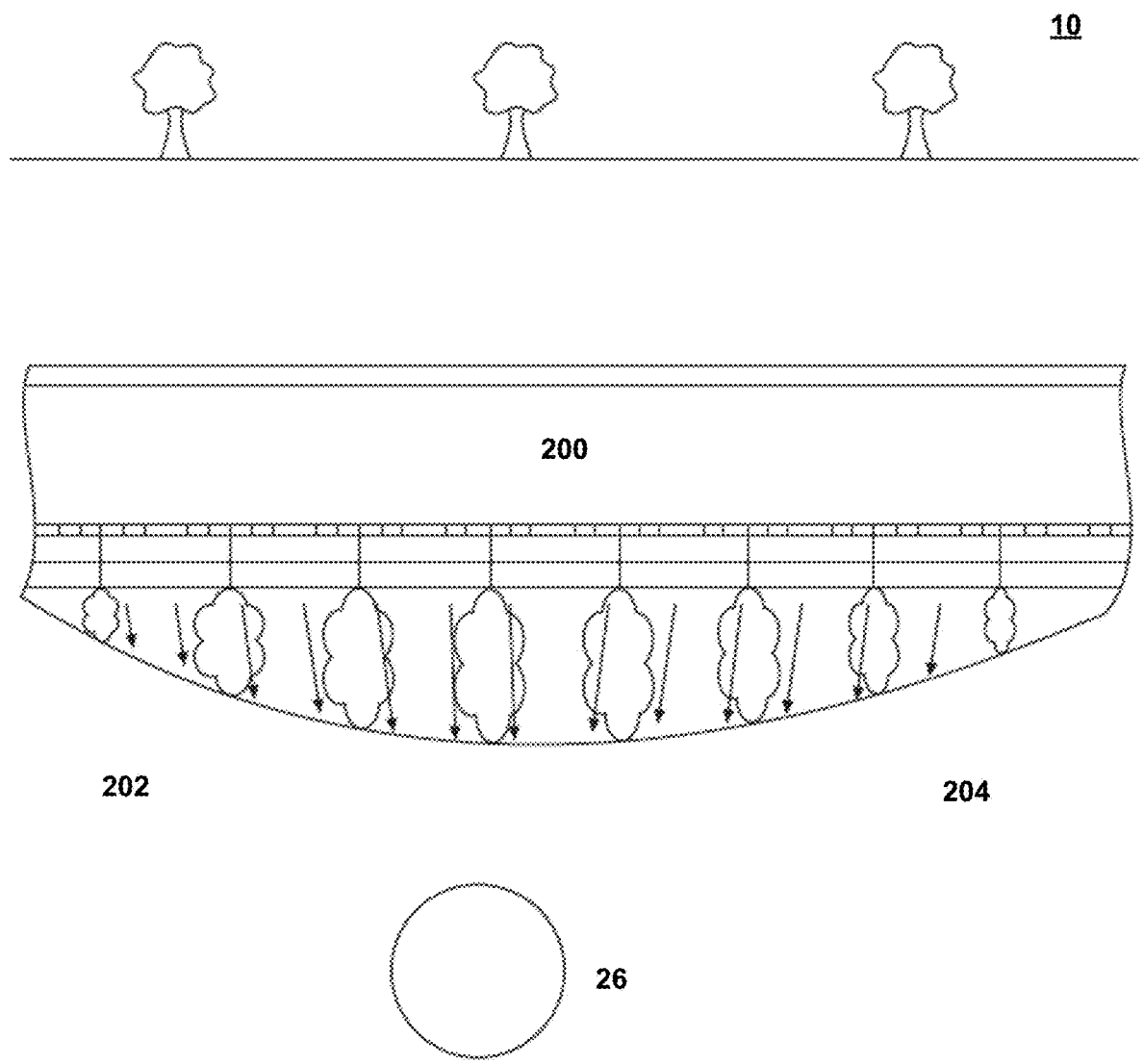
FIG. 19 is a schematic depicting an example of a new tunnel being constructed beneath an existing building where the process allows for real-time direct intervention from the asset to be protected (e.g., from within a building or within a tunnel) in accordance with an embodiment of the present disclosure.

FIG. 19 shows new tunnel 26 being constructed beneath existing railway tunnel 200. In this example, process 10 for real-time displacement control using expansive grouts is introduced via injection boreholes 202 which are drilled from the existing tunnel. The displacement caused by process 10 for real-time displacement control using expansive grouts in this example is exemplified by profile of soil displacement 204 (scale exaggerated).

Figure 20:
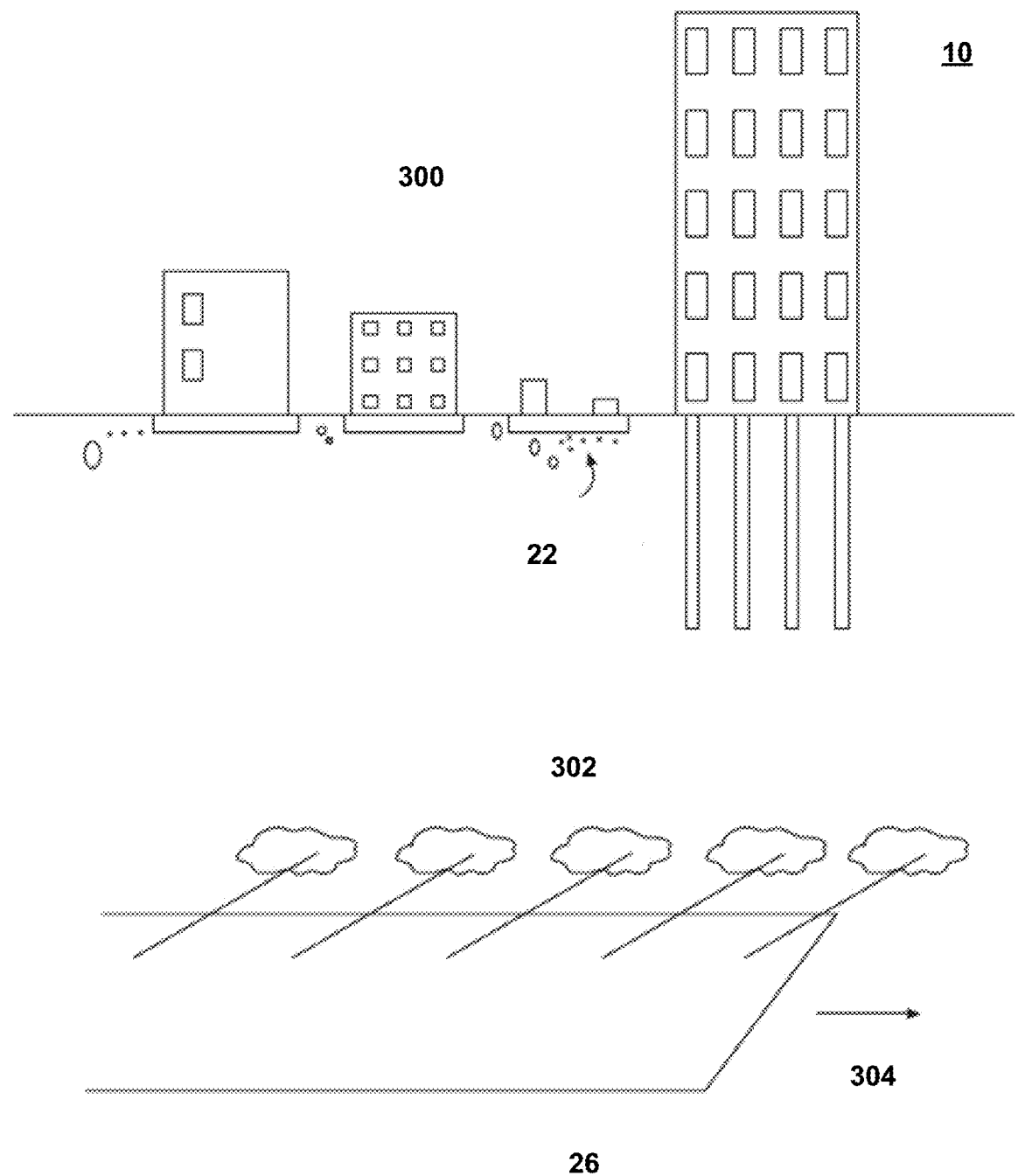
FIG. 20 is a schematic depicting an example of a new tunnel being constructed beneath an existing building where the process allows for real-time direct intervention from the asset to be protected (e.g., from within a building or within a tunnel) in accordance with an embodiment of the present disclosure.

FIG. 20 shows new tunnel 26 being constructed beneath existing buildings 300, which may include existing utilities 22. In this example, process 10 for real-time displacement control using expansive grouts is introduced via injection boreholes 302 which are drilled from new tunnel 26 under construction in a specific direction (i.e. drive direction 304).

Figure 21:
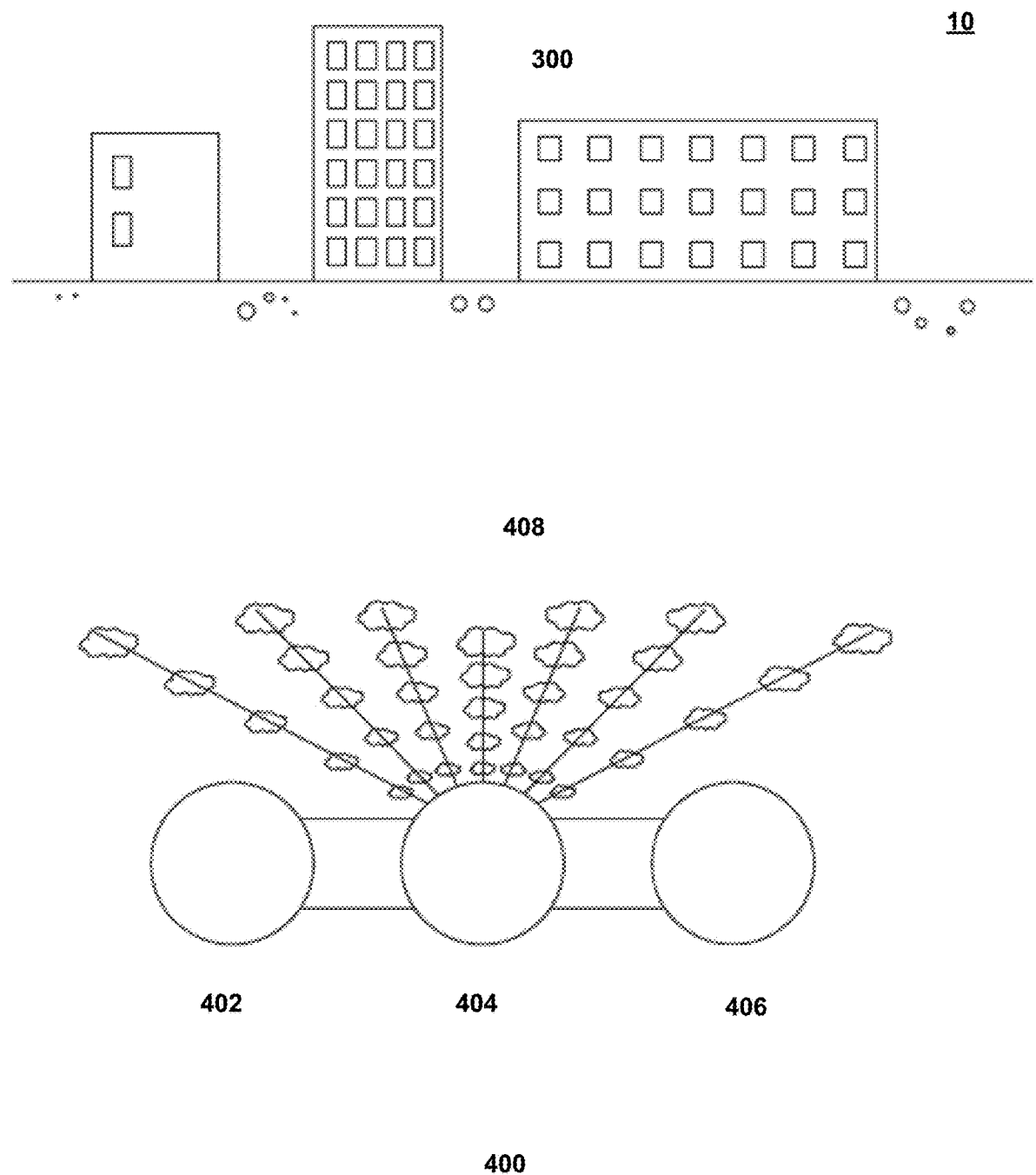
FIG. 21 is a schematic depicting an example of a new underground station being constructed beneath an existing building in accordance with an embodiment of the present disclosure.

FIG. 21 shows a new underground station 400 being constructed beneath existing buildings 300, where new underground station 400 may include platform 402, concourse 404, and platform 406. In this example, process 10 for real-time displacement control using expansive grouts is introduced via injection boreholes 408 which are drilled from a first tunnel to be constructed. Injection boreholes 408 may also be inclined forwards so as to provide real-time displacement control for the construction of the first tunnel as well as subsequent tunnels, junctions and cross passages.

Figure 22:
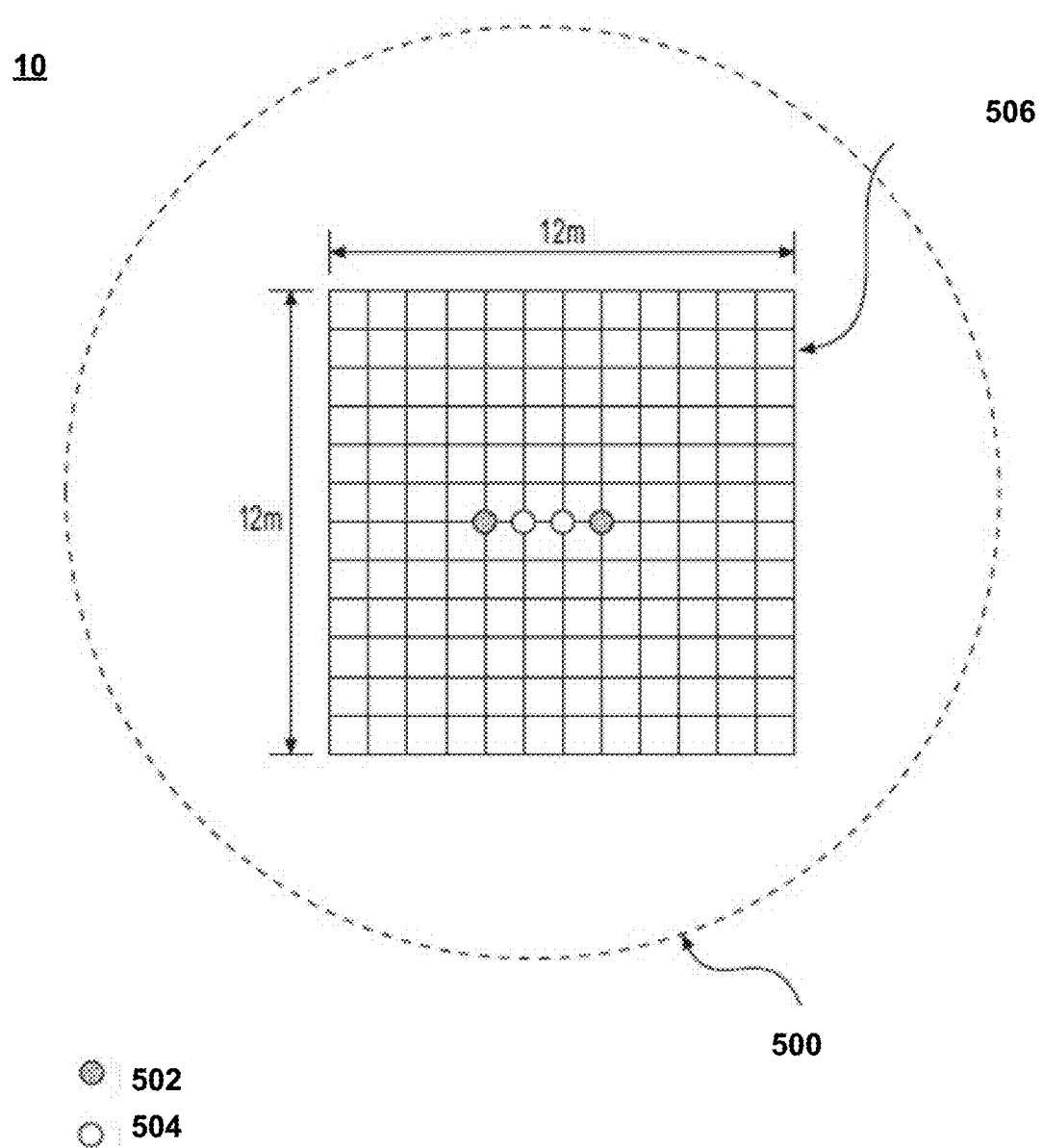
FIG. 22 is a schematic depicting the proof of concept trial that was undertaken in accordance with an embodiment of the present disclosure.
Figure 23:
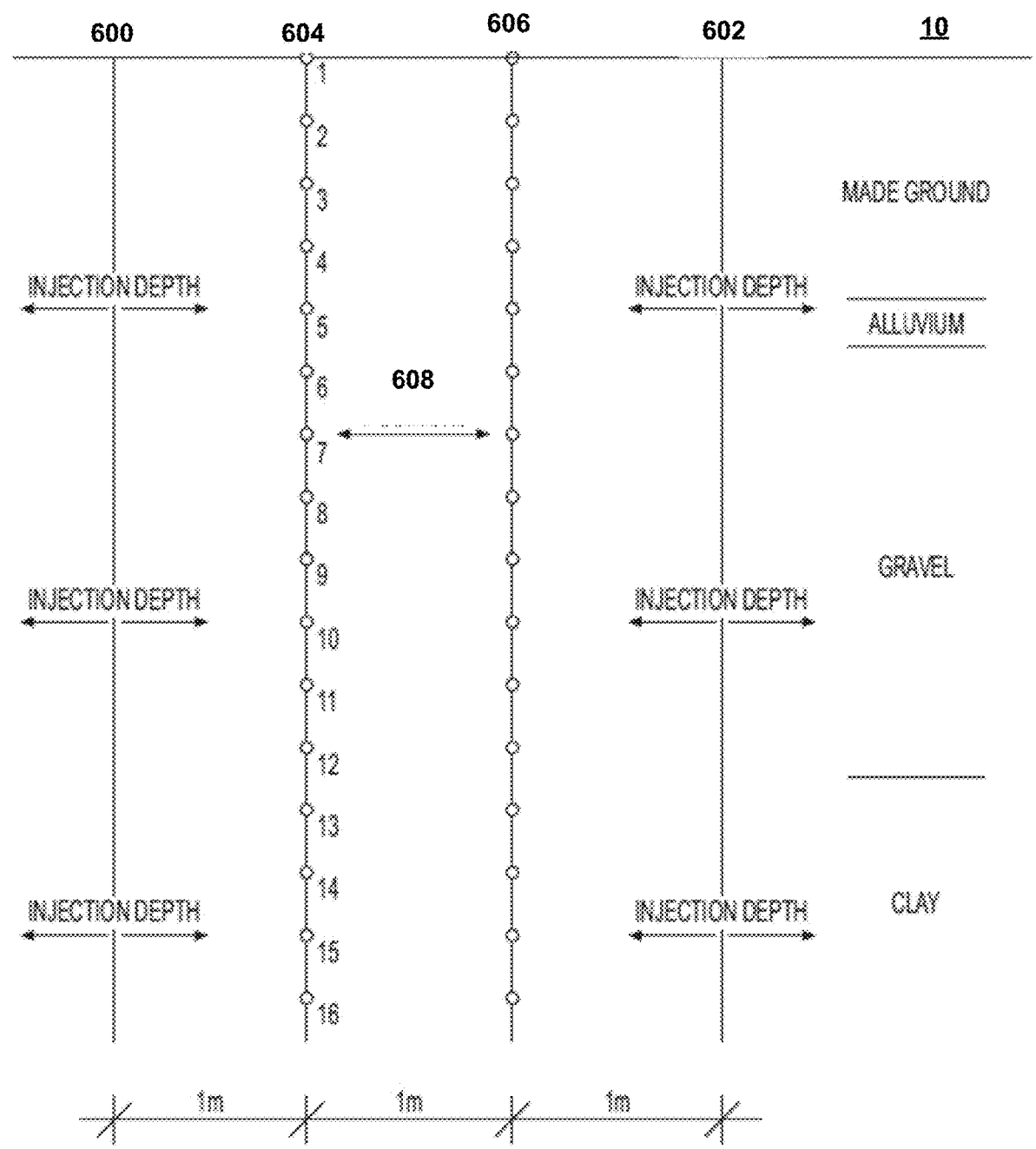
FIG. 23 is a schematic depicting the injection and monitoring boreholes that were used in the proof of concept trial in accordance with an embodiment of the present disclosure.

FIGS. 22 and 23 show a proof of concept trial undertaken to demonstrate the effectiveness of process 10 for real-time displacement control using expansive grouts. The embodiment depicted in FIG. 22 shows the perimeter of a 30 m diameter deep shaft to be constructed following the trial of process 10 for real-time displacement control using expansive grouts (i.e. perimeter 500). Injection boreholes 502 are shown in darkened circles and fiber optic monitoring boreholes 504 are shown in the undarkened circles. Further, array 506 shows the distribution of surface monitoring.

Referring also, to FIG. 23, an embodiment consistent with the teachings of the present disclosure is provided. A plurality of injection points were installed in injection boreholes 600 and 602 (i.e. borehole 1 (BH1) and borehole 2 (BH2), respectively) installed in a pre-determined configuration some 3 m apart and extending 15 m below the ground surface. These injection boreholes were used for injecting expansive grout at 4 m, 9 m and 14 m below ground level. Four tubes (e.g., 12 mm outer diameter) were installed in BH1 and BH2 at each depth (in total 12 tubes per borehole).

Two monitoring boreholes, monitoring borehole 604 (hereinafter "M1") and monitoring borehole 606 (hereinafter "M2") were installed in between the two injection boreholes as shown in FIG. 23. The monitoring boreholes were fitted with highly accurate fiber optic measuring instrumentation 608 capable of measuring axial strain at each of the sensor locations (spaced at vertical 1 m intervals). These instruments were able to measure ground strains before; during and after each injection campaign in the adjacent injection boreholes. Once the data was obtained it was transmitted to a computing device such as those depicted in FIG. 27.

As discussed above, this monitoring may use any suitable monitoring device 111. While this trial utilized Fiber Bragg Grating Sensing cables, and Fiber Bragg Grating Interrogators it should be noted that these devices are provided merely by way of example and numerous other devices may be used without departing from the scope of the present disclosure.

In addition to the measurement of sub-surface ground strains, surface displacements caused by the injection of the expansive grouts were also recorded on the surface array using a total station instrument (0.5 second accuracy) and a rotating laser (accuracy±1 mm).

The trial utilized one vehicle containing a double pumping set up, which allowed for the injection of two tubes simultaneously, while minimizing the footprint of the work area that is required. Heated supply hoses were connected from two drums of material (e.g., a resin and a hardener, located on the truck) to an injection gun. The injection gun was connected to the tubing, forming a complete seal. Before any material is pumped, a material quality test was carried out to confirm the geopolymer is of the correct consistency. If it was not, the gauges and pumps were altered until it is. In some embodiments, the material may be pumped from a proportioner (e.g., heater and pump) in short duration bursts, from the heated hoses to where it is being injected. During the injection process the material may expand up to 20 times its liquid volume and exert an expansive force. As the material expands, it may compact the surrounding soils and/or displaces it. At each injection depth a set volume of material was injected, however, the injection process may be halted if excessive surface movement was detected by the digital monitors positioned close to the injection point. After each injection the tubes were cut off at surface level to prevent any trip hazards.

The proof of concept trial explored the relative performance of "top down" and "bottom up" injection strategies and examined the effects of injecting expanding grouts with both fast and slow setting times. It satisfactorily demonstrated that the process can overcome a number of the technological uncertainties that existed prior to the trial. These being the ability of the expansive grouts to fracture stiff and competent ground conditions; the ability to enable multiple injections to be performed at the same point via the plurality of injection pipes installed at each injection depth and finally the ability to utilize grouts of different setting times to first strengthen the ground and then to displace the ground.

The proof of concept trial was a complete success and provided invaluable data that will be used to enable the planning and design of future schemes.

Figure 24:
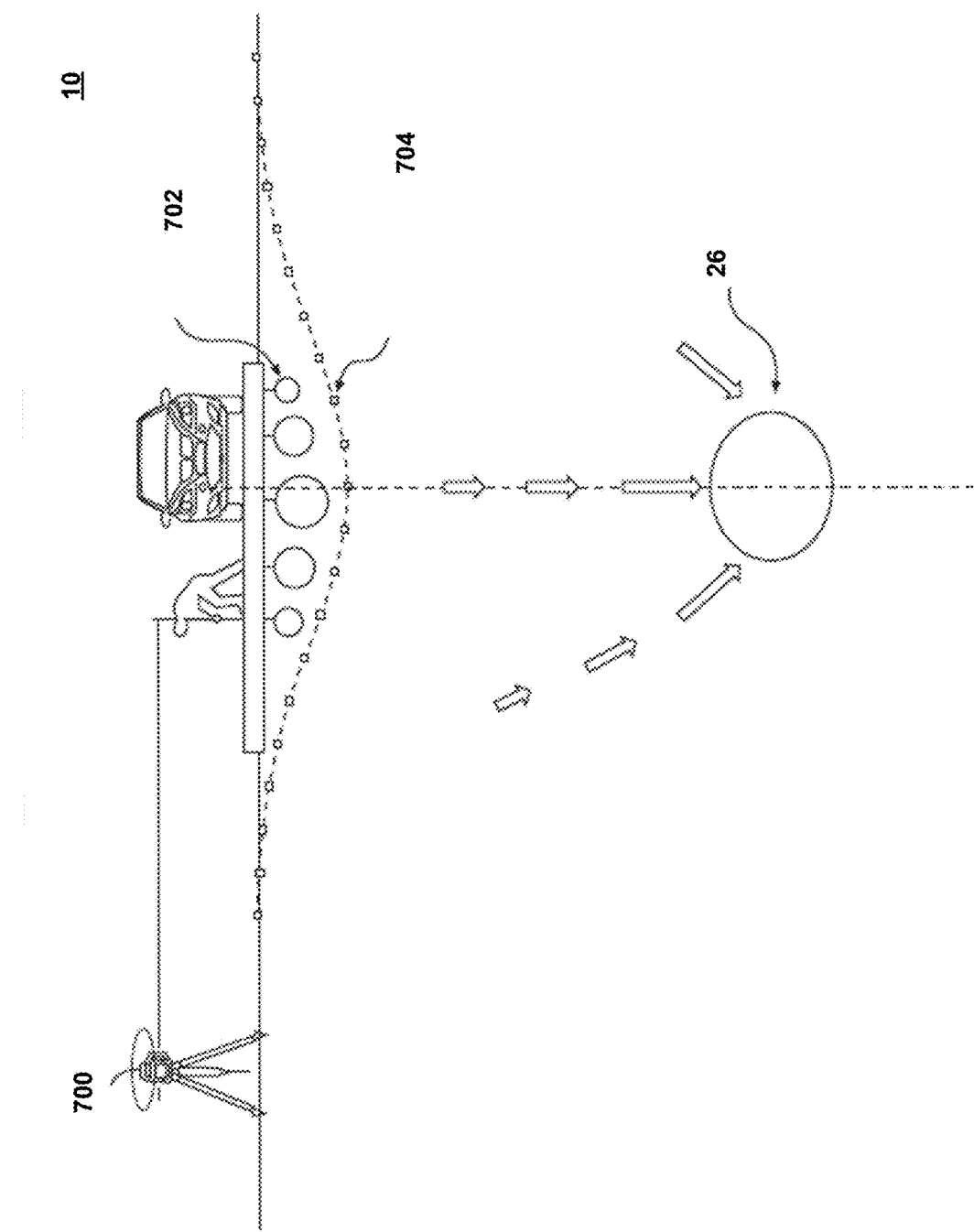
FIG. 24 is a schematic depicting an example of road levelling whilst monitoring using a rotating laser in accordance with an embodiment of the present disclosure.
Figure 25:
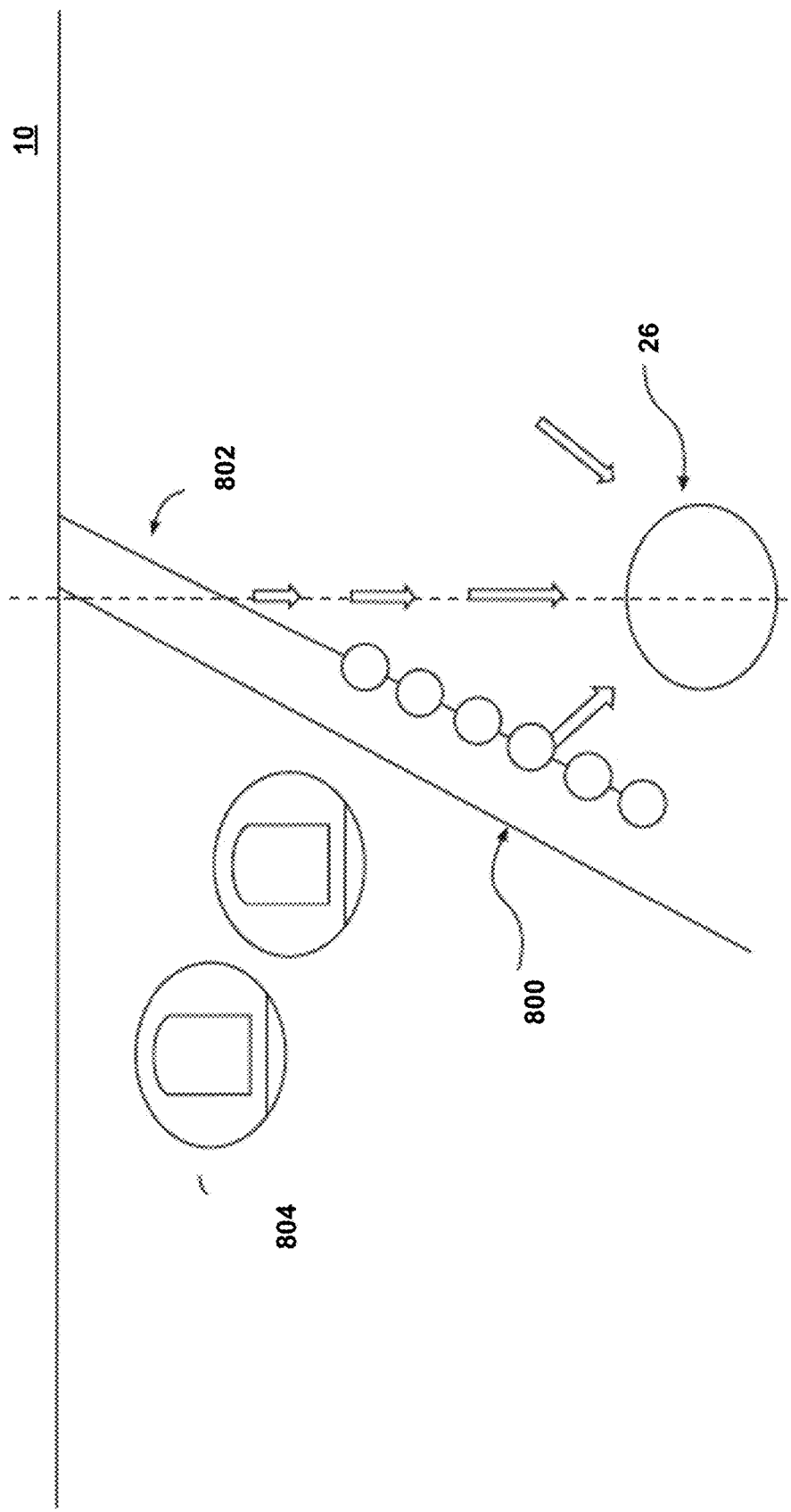
FIG. 25 is a schematic depicting an example including one or more borehole instruments used to measure sub-surface displacements in accordance with an embodiment of the present disclosure.
Figure 26:
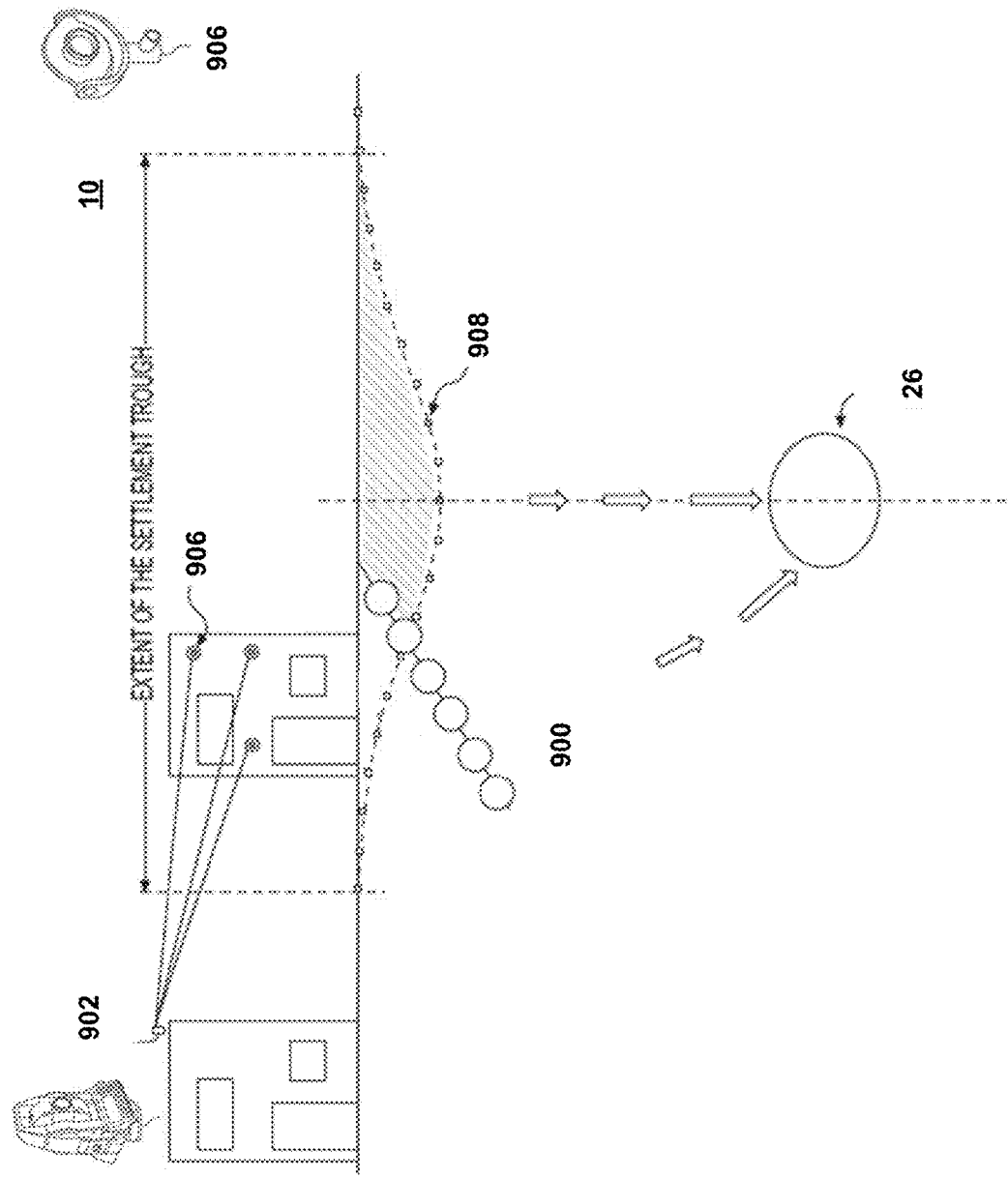
FIG. 26 is a schematic depicting an example of a geodetic monitoring arrangement in accordance with an embodiment of the present disclosure.

Referring now to FIGS. 24-26, embodiments consistent with the real-time displacement control process 10 described herein. FIG. 24 shows an example of new tunnel 26 being constructed and road levelling whilst monitoring using rotating laser 700. As is shown in the Figure, expansive grout, such as those discussed herein, may be injected beneath the road slab as the settlement from the tunnel construction occurs via expansive grout injection boreholes 702. The road level may be monitored using surveying techniques, some of which may include, but are not limited to, rotating lasers, water level, optical level, and/or a total station. The settlement caused by the construction of new tunnel 26 by process 10 for real-time displacement control using expansive grouts in this example is exemplified the ground settlement profile 704 (scale exaggerated).

Referring also to FIG. 25, an embodiment consistent with process 10 for real-time displacement control using expansive grouts in construction of new tunnel 26 is provided. One or more borehole instruments 800 may be used to measure sub-surface displacements, and specifically to measure ground movement between injection boreholes 802, which may be expansive grout injection boreholes, and existing metro tunnels 804. Some of these may include, but are not limited, to rod extensometers, inclinometers, fiber optic instruments, etc. In operation, if the grout injection strategy is successful borehole instruments 800 should measure very little movement. Comprehensive ground displacement information may be obtained by using a combination of instruments. Further, the bottom of borehole instruments 800 should preferably be anchored in a zone that is not within the movement zone.

In some embodiments, a continuous rod extensometer system may be configured to accurately measure settlement and/or heave at single or multiple anchor points in a borehole and at its reference head. The system may employ up to eight rods, anchored along the axis of a borehole, terminating in the reference head at the borehole entrance. Displacement along the axis of the borehole from the anchor may be recorded by measuring movement of the top of the rod relative to the reference head. The continuous rod extensometer may be pre-assembled to specified lengths. Some options for continuous rod extensometers may include, but are not limited to, automatic or manual reading, hydraulic anchoring for soil, groutable anchoring for rock, multiple or single point rod reference, etc.

In some embodiments, a digital inclinometer system may be used to measure lateral deflections within a borehole. The system comprises a biaxial probe, cable reel and ultra-rugged Field PC supplied with "in-port" data capture software. The probe provides accurate and repeatable readings transferred via a digital signal. Wireless communication options enable a cable free data transmitting system with no connectors to corrode or break. The cable may include a cable marker system which, when used in conjunction with the cable gate, may provide highly accurate and repeatable depth control. The vertical digital inclinometer system is a robust and highly accurate system that is light, compact, and easy to operate in any environment.

In some embodiments, a fiber optic sensor may use optical fiber either as a sensing element ("intrinsic sensors"), or as means of relaying signals from a remote sensor to the electronics that process the signals ("extrinsic sensors"). Fibers have many uses in remote sensing. Depending upon configuration they can measure either axial or bending strain.

Referring now to FIG. 26, an embodiment consistent with process 10 for real-time displacement control using expansive grouts where new tunnel 26 is being constructed is provided. This embodiment depicts an example geodetic monitoring arrangement. As shown in the figure, multiple injection boreholes 900 may be installed to protect existing building 20 within the settlement zone of influence where settlement beneath existing building 20 would be reduced or eliminated by the injection of the expansive grout and needs to be protected from the settlement. Multiple injections may be required at each depth as the settlement develops as the tunnel passes. Automated total station 902 may be positioned aboveground outside of the settlement zone of influence (i.e. permanently fixed to existing building 904). If this is not possible then the instrument may need to recalibrate its position by use of reference targets, which are outside the zone of influence. Automated total station 902 may take a round of readings to multiple targets on multiple buildings. The frequency of readings may depend upon the anticipated rate of settlement. In some cases, the reading frequency may be set at less than one hour. The data may be stored on a data-logger and may be transferred to the monitoring engineer's computer for analysis. This may occur via a hard wired or wireless system. The monitoring engineer may process the data and transfer this to a grouting crew so that they may determine the next grouting campaign. The time between taking the reading and this being available to the grouting crews may be determined before work commences. In certain circumstances where the rate of settlement is anticipated to be high it may be necessary for this transfer to be "real-time" with zero delay. Further, optical prism 906 may be used in this embodiment, where optical prism 906 is located aboveground and affixed to existing building 20. The settlement caused by the construction of new tunnel 26 by process 10 for real-time displacement control using expansive grouts in this example is exemplified the ground settlement profile 908 (scale exaggerated). Additionally, the magnitude of the ground movement is proportional to the distance from new tunnel 26 and the largest movements will occur immediately adjacent to new tunnel 26.

Figure 27:
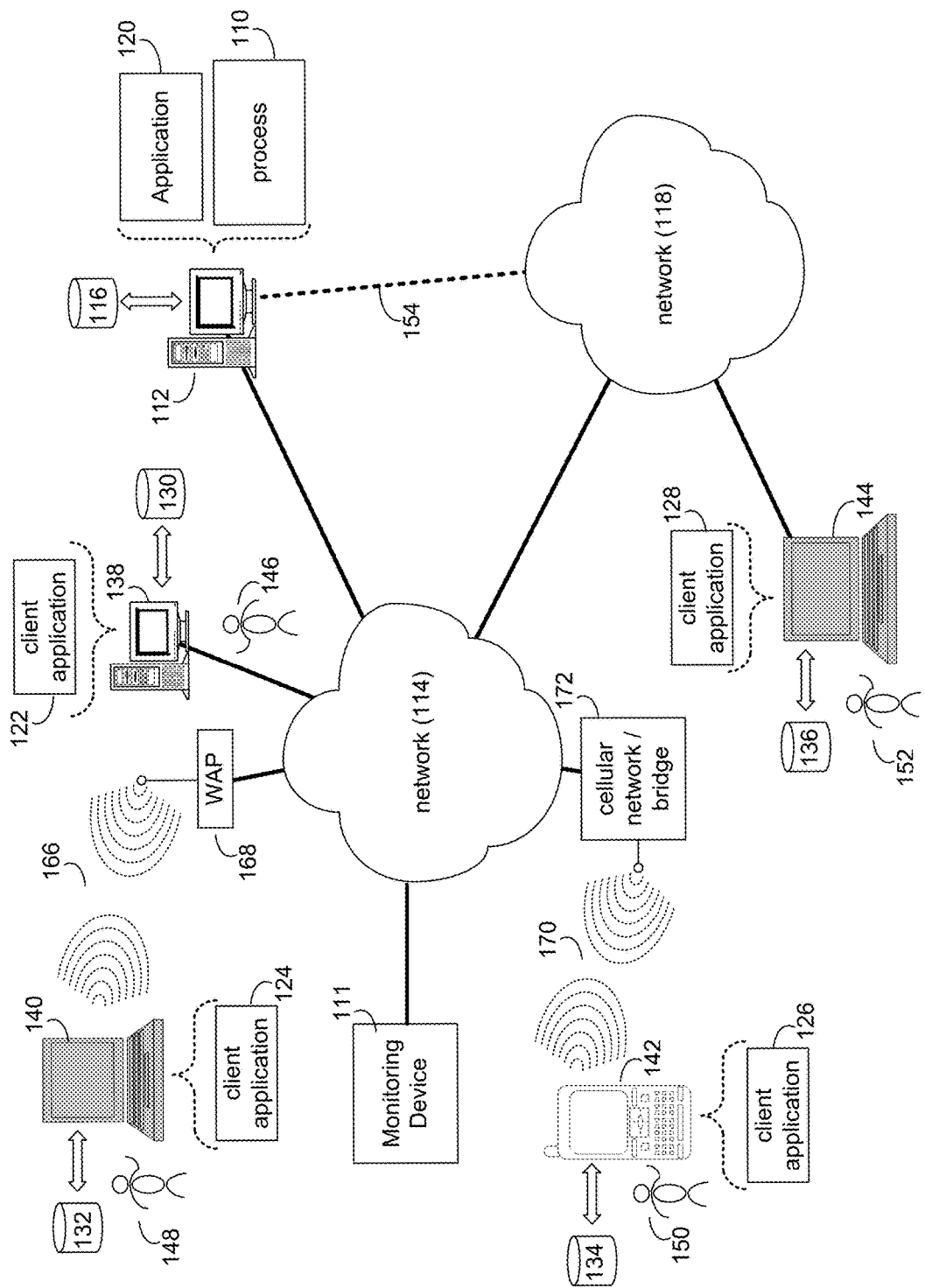
FIG. 27 is a system diagram depicting a computing environment that may be configured to receive monitoring data from the processes described herein.

Referring to FIG. 27, there is shown a process 110 that may reside on and may be executed by server computer 112, which may be connected to network 114 (e.g., the Internet or a local area network). Process 110 may be configured to receive real-time monitoring data from any or all of the monitoring devices 111 associated with the construction processes described herein. Examples of server computer 112 may include, but are not limited to: a personal computer, a server computer, a series of server computers, a mini computer, and a mainframe computer. Server computer 112 may be a web server (or a series of servers) running a network operating system, examples of which may include but are not limited to: Microsoft® Windows® Server; Novell® NetWare®; or Red Hat® Linux®, for example. (Microsoft and Windows are registered trademarks of Microsoft Corporation in the United States, other countries or both; Novell and NetWare are registered trademarks of Novell Corporation in the United States, other countries or both; Red Hat is a registered trademark of Red Hat Corporation in the United States, other countries or both; and Linux is a registered trademark of Linus Torvalds in the United States, other countries or both.) Additionally/alternatively, the process may reside on and be executed, in whole or in part, by a client electronic device, such as a personal computer, notebook computer, personal digital assistant, or the like.

The instruction sets and subroutines of process 110, which may include one or more software modules, and which may be stored on storage device 116 coupled to server computer 112, may be executed by one or more processors (not shown) and one or more memory modules (not shown) incorporated into server computer 112. Storage device 116 may include but is not limited to: a hard disk drive; a solid state drive, a tape drive; an optical drive; a RAID array; a random access memory (RAM); and a read-only memory (ROM). Storage device 116 may include various types of files and file types.

Server computer 112 may execute a web server application, examples of which may include but are not limited to: Microsoft IIS, Novell Webserver™, or Apache® Webserver, that allows for HTTP (e.g., HyperText Transfer Protocol) access to server computer 112 via network 114 (Webserver is a trademark of Novell Corporation in the United States, other countries, or both; and Apache is a registered trademark of Apache Software Foundation in the United States, other countries, or both). Network 114 may be connected to one or more secondary networks (e.g., network 118), examples of which may include but are not limited to: a local area network; a wide area network; or an intranet, for example.

Server computer 112 may execute an application 120, examples of which may include, but are not limited to those available from the assignee of the present application. application 120 may interact with one or more client applications (e.g., client applications 122, 124, 126, 128).

Process 110 may be a stand-alone application, or may be an applet/application/script that may interact with and/or be executed within application 120. In addition/as an alternative to being a server-side process, the process may be a client-side process (not shown) that may reside on a client electronic device (described below) and may interact with an client application (e.g., one or more of client applications 122, 124, 126, 128). Further, the process may be a hybrid server-side/client-side process that may interact with application 120 and a client application (e.g., one or more of client applications 122, 124, 126, 128). As such, the process may reside, in whole, or in part, on server computer 112 and/or one or more client electronic devices. Accordingly, any or all of these devices may be configured to display, at a graphical user interface, at least a portion of the real-time monitoring data.

The instruction sets and subroutines of application 120, which may be stored on storage device 116 coupled to server computer 112 may be executed by one or more processors (not shown) and one or more memory modules (not shown) incorporated into server computer 112.

The instruction sets and subroutines of client applications 122, 124, 126, 128, which may be stored on storage devices 130, 132, 134, 136 (respectively) coupled to client electronic devices 138, 140, 142, 144 (respectively), may be executed by one or more processors (not shown) and one or more memory modules (not shown) incorporated into client electronic devices 138, 140, 142, 144 (respectively). Storage devices 130, 132, 134, 136 may include but are not limited to: hard disk drives; solid state drives, tape drives; optical drives; RAID arrays; random access memories (RAM); read-only memories (ROM), compact flash (CF) storage devices, secure digital (SD) storage devices, and a memory stick storage devices. Examples of client electronic devices 138, 140, 142, 144 may include, but are not limited to, personal computer 138, laptop computer 140, mobile computing device 142 (such as a smart phone, netbook, or the like), notebook computer 144, for example. Using client applications 122, 124, 126, 128, users 146, 148, 150, 152 may access application 120 and may allow users to e.g., utilize process 110.

Users 146, 148, 150, 152 may access application 120 directly through the device on which the client application (e.g., client applications 122, 124, 126, 128) is executed, namely client electronic devices 138, 140, 142, 144, for example. Users 146, 148, 150, 152 may access application 120 directly through network 114 or through secondary network 118. Further, server computer 112 (e.g., the computer that executes application 120) may be connected to network 114 through secondary network 118, as illustrated with phantom link line 154.

In some embodiments, process 110 may be a cloud-based process as any or all of the operations described herein may occur, in whole, or in part, in the cloud or as part of a cloud-based system. The various client electronic devices may be directly or indirectly coupled to network 114 (or network 118). For example, personal computer 138 is shown directly coupled to network 114 via a hardwired network connection. Further, notebook computer 144 is shown directly coupled to network 118 via a hardwired network connection. Laptop computer 140 is shown wirelessly coupled to network 114 via wireless communication channel 166 established between laptop computer 140 and wireless access point (e.g., WAP) 168, which is shown directly coupled to network 114. WAP 168 may be, for example, an IEEE 802.11a, 802.11b, 802.11g, Wi-Fi, and/or Bluetooth device that is capable of establishing wireless communication channel 166 between laptop computer 140 and WAP 168. Mobile computing device 142 is shown wirelessly coupled to network 114 via wireless communication channel 170 established between mobile computing device 142 and cellular network/bridge 172, which is shown directly coupled to network 114.

As is known in the art, all of the IEEE 802.11x specifications may use Ethernet protocol and carrier sense multiple access with collision avoidance (e.g., CSMA/CA) for path sharing. The various 802.11x specifications may use phase-shift keying (e.g., PSK) modulation or complementary code keying (e.g., CCK) modulation, for example. As is known in the art, Bluetooth is a telecommunications industry specification that allows e.g., mobile phones, computers, and personal digital assistants to be interconnected using a short-range wireless connection.

Client electronic devices 138, 140, 142, 144 may each execute an operating system, examples of which may include but are not limited to Microsoft Windows, Microsoft Windows CE®, Red Hat Linux, or other suitable operating system. (Windows CE is a registered trademark of Microsoft Corporation in the United States, other countries, or both).

As will be appreciated by one skilled in the art, the present disclosure may be embodied as a method, system, or computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer readable medium may be a computer readable signal medium or a computer readable storage medium. A computer-usable, or computer-readable, storage medium (including a storage device associated with a computing device or client electronic device) may be, for example, but not limited to, an electronic, magnetic, optical, electromagnetic, infrared, or semiconductor system, apparatus, or device, or any suitable combination of the foregoing. More specific examples (a non-exhaustive list) of the computer-readable medium would include the following: an electrical connection having one or more wires, a portable computer diskette, a hard disk, a random-access memory (RAM), a read-only memory (ROM), an erasable programmable read-only memory (EPROM or Flash memory), an optical fiber, a portable compact disc read-only memory (CD-ROM), an optical storage device. In the context of this document, a computer-usable, or computer-readable, storage medium may be any tangible medium that can contain, or store a program for use by or in connection with the instruction execution system, apparatus, or device.

A computer readable signal medium may include a propagated data signal with computer readable program coded embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable medium may be transmitted using any appropriate medium, including but not limited to wireless, wireline, optical fiber cable, RF, etc., or any suitable combination of the foregoing.

Computer program code for carrying out operations of the present disclosure may be written in an object-oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present disclosure is described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

In some cases, the features disclosed in this application may be used as such, irrespective of other features. On the other hand, when necessary, the features disclosed in this application may be combined to provide various combinations.

It will be obvious to a person skilled in the art that as technology advances, the basic idea of the invention may be implemented in a plurality of ways. The invention and its embodiments are thus not restricted to the examples described above but may vary within the scope of the claims.

It will be apparent to those skilled in the art that various modifications and variations can be made in the embodiments of the present disclosure without departing from the spirit or scope of the present disclosure. Thus, it is intended that embodiments of the present disclosure cover the modifications and variations provided they come within the scope of the appended claims and their equivalents.

What is claimed is:

1. A method for real-time compensation for ground movements which would otherwise adversely affect an existing built environment comprising:
   providing a plurality of holes in soil for the injection of a substance that expands as a consequence of a chemical reaction, wherein the plurality of holes are located between an activity that is causing ground movements and an asset to be protected;
   injecting, in at least one of the plurality of holes, the substance in real-time, wherein the injecting occurs during the activity that is causing the ground movements and mitigates the impact of the ground movements on the asset to be protected, wherein the activity that is causing the ground movements includes subterranean construction adjacent to the asset to be protected;
   monitoring, in real-time, a level of the soil, wherein the real-time monitoring occurs during the activity that is causing the ground movements;
   obtaining real-time monitoring data, based upon, at least in part, the monitoring, wherein obtaining the real-time monitoring data includes determining when the level of the soil begins to rise and accurately detecting an amount of lifting in the soil; and
   controlling the lifing of the soil in real-time using, at least in part, the obtained real-time monitoring data.

2. The method of claim 1, further comprising:
   displaying, at a graphical user interface, at least a portion of the real-time monitoring data.

3. The method of claim 1, wherein the monitoring includes monitoring at least one of displacement, stress, strain or temperature.

4. The method of claim 1, wherein the monitoring includes taking measurements prior to the injecting the substance.

5. The method of claim 1, wherein the monitoring includes taking measurements during the injecting the substance.

6. The method of claim 1, wherein the monitoring includes taking measurements after the injecting the substance.

7. The method of claim 1, further comprising:
adjusting, in real-time, the injecting based upon, at least in part, the monitoring in real-time.

8. The method of claim 1, further comprising:
installing above ground instrumentation to measure movement of the ground.

9. The method of claim 1, further comprising:
installing below ground instrumentation to measure movement of the ground, wherein the below ground instrumentation includes a plurality of sensors that measure axial strain, the plurality of sensors are located in at least one monitoring borehole.

10. The method of claim 1, further comprising:
transmitting, from at least one measurement instrument to a computing device, the real-time monitoring data associated with the injection of the expanding substance.

11. The method of claim 1, wherein providing the plurality of holes includes installing a plurality of injection boreholes in a pre-determined configuration.

12. The method of claim 1, further comprising:
selecting the substance, wherein the substance is selected from the group consisting of a polymer, an expanding resin or an organically incrystallizable, chemically expanding multicomponent substance.

13. The method of claim 1, further comprising:
preparing a mitigation strategy in advance of the activity.

14. The method of claim 1, further comprising:
selecting an injection strategy compatible with ground conditions or a ground movement mitigation strategy.

15. The method of claim 1, further comprising:
inserting an expansion element into at least one of the plurality of holes; and
reacting the substance in the expansion element in the at least one of the plurality of holes.

16. The method of claim 1, further comprising monitoring, in real-time, an asset to be protected.

17. The method of claim 1, wherein the distance between the plurality of holes is ocnfigured to be about 0.5 m to about 3.

18. The method oc claim 1, wherein the substance has a density ranging between about 100 kg/m$^3$ and about 800 kg/m$^3$.

19. A construction method comprising:
drilling a plurality of holes in a predetermined location;
injecting, in at least one of the plurality of holes, a substance in real-time that expands as a consequence of a chemical reaction, wherein the injecting occurs during an activity that is causing the ground movements and mitigates the impact of the ground movements on an asset to be protected, wherein the activity that is causing the ground movements includes subterranean construction adjacent to the asset to be protected;
monitoring, in real-time, during at least one of the injecting or expansion of the substance, movement associated with the predetermined location, wherein the monitoring occurs during an activity that is causing the ground movements;
obtaining real-time monitoring data, based upon, at least in part, the monitoring, wherein obtaining the real-time monitoring data includes determining when a level of the soil begins to rise and accurately detecting an amount of lifting in the soil;
controlling the lifting of the soil in real-time using, at least in part, the obtained real-time monitoring data; and
transmitting monitoring data, based upon, at least in part, the monitoring.

20. The method of claim 19, further comprising:
inserting one or more injection tubes into each of the plurality of holes.

21. The method of claim 20, wherein the one or more injection tubes have an inner diameter of 10 mm.

22. The method of claim 20, wherein the one or more injection tubes are comprised of one or more of metal and plastic.

23. The method of claim 22, wherein the metal comprising the one or more injection tubes is steel.

24. The method of claim 20, wherein the one or more injection tubes include a wall comprised of one or more textile reinforcements.

25. The method of claim 24, wherein the one or more textile reinforcements are comprised of one or more of a fabric and a metal.

26. The method of claim 19, further comprising:
displaying, at a graphical user interface, at least a portion of the monitoring data.

27. The method of claim 19, wherein the monitoring includes monitoring at least one of displacement, stress, strain or temperature.

28. The method of claim 19, further comprising:
adjusting, in real-time, the injecting based upon, at least in part, the monitoring.

29. The method of claim 19, wherein the substance is comprised of, at least in part, an organically incrystallizable, chemically expanding multicomponent substance.

* * * * *